(12) United States Patent
Opalsky et al.

(10) Patent No.: US 6,438,498 B1
(45) Date of Patent: Aug. 20, 2002

(54) SYSTEM, METHOD AND COMPUTER IMPLEMENTED PROCESS FOR ASSAYING COAGULATION IN FLUID SAMPLES

(75) Inventors: Cindra A. Widrig Opalsky; David Opalsky, both of Ottawa; Andy Maczuszenko, Etobicoke; Imants R. Lauks, Rockcliffe Park, all of (CA)

(73) Assignee: I-Stat Corporation, East Windsor, NJ (US)

( * ) Notice: Subject to any disclaimer, the term of this patent is extended or adjusted under 35 U.S.C. 154(b) by 0 days.

(21) Appl. No.: 09/528,238

(22) Filed: Mar. 17, 2000

Related U.S. Application Data
(60) Provisional application No. 60/181,544, filed on Feb. 10, 2000.

(51) Int. Cl.[7] .............................................. G01N 31/00
(52) U.S. Cl. .............................. 702/25; 702/22; 435/6; 435/7.1
(58) Field of Search ........................ 702/22, 25, 30–32, 702/100, 104, 189; 73/864.21, 864.22, 864.24; 422/63, 73, 81, 100; 435/6, 7.1, 7.4, 13

(56) References Cited

U.S. PATENT DOCUMENTS

| 4,304,853 | A | | 12/1981 | Jozefonvicz et al. |
| 4,497,744 | A | | 2/1985 | Fawzi |
| 4,756,884 | A | | 7/1988 | Hillman et al. |
| 4,764,342 | A | * | 8/1988 | Kelln et al. .................... 422/72 |
| 5,096,669 | A | | 3/1992 | Lauks et al. |
| 5,163,131 | A | | 11/1992 | Row et al. |
| 5,200,051 | A | | 4/1993 | Cozzette et al. |
| 5,302,348 | A | | 4/1994 | Cusack et al. |
| 5,447,440 | A | | 9/1995 | Davis et al. |
| 5,526,111 | A | | 6/1996 | Collins et al. |
| 5,534,226 | A | | 7/1996 | Marcelino et al. |
| 5,558,838 | A | * | 9/1996 | Uffenheimer ................ 422/63 |
| 5,628,961 | A | | 5/1997 | Davis et al. |
| 5,731,212 | A | | 3/1998 | Gavin et al. |
| 5,895,869 | A | * | 4/1999 | Von Behrens et al. ..... 73/865.5 |
| 5,916,522 | A | | 6/1999 | Boyd et al. |
| 5,919,711 | A | | 7/1999 | Boyd et al. |
| 6,016,712 | A | * | 1/2000 | Warden et al. ........... 73/864.21 |

OTHER PUBLICATIONS

Janene Keeth, et al., "A Clinical Evaluation of the HemoTec ACT", Proceedings of the American Academy of Cardiovascular Perfusion, vol. 9, Sep. 1988, pp. 22–25.
Luiz Andre Barroso, et al., "RPM: A Rapid Prototyping Engine for Multiprocessor Systems", IEEE Spectrum, 1995, pp. 26–34.
Zorbas, Y. G., et al.,, "Heparin Effect on Blood Clotting and Coagulation of Vasular Wall Under Hypokinesia", abstract.
Aaron Boxer, "Where Buses Cannot Go", IEEE Spectrum, Feb. 1995, pp. 41–45.

* cited by examiner

Primary Examiner—Bryan Bui
(74) Attorney, Agent, or Firm—Katten Muchin Zavis Rosenman; Gilberto M. Villacorta

(57) ABSTRACT

A sample analyzing system includes at least one sensor located at least partially within a sample retaining area. In addition, the sensor has at least one edge defining a sample detection location. This sample detection location defines an area within which the sensor is capable of detecting a presence or an absence of the sample. The system analyzes sample data by first introducing the sample into the sample retaining area and then mixing a reagent with the sample to commence formation of a reagent product. After mixing and upon detecting the absence of the sample from the sample detection location by the at least one sensor, an edge of the sample is moved past an edge of the at least one sensor and into the sample detection location. Then, upon detecting the presence of the sample in the sample detection location by the at least one sensor, the edge of the sample is moved past the edge of the at least one sensor and out of the sample detection location. Additionally, between oscillations, data may be collected by one or more sensors. By repeating these steps, an accumulation of material on or about the at least one sensor may be prevented.

47 Claims, 13 Drawing Sheets

SYSTEM, METHOD AND COMPUTER IMPLEMENTED PROCESS FOR ASSAYING COAGULATION IN FLUID SAMPLES

RELATED APPLICATIONS

This application claims priority from U.S. Provisional Application No. 60/181,544 filed Feb. 10, 2000, incorporated herein by reference.

FIELD OF THE INVENTION

The present invention relates to a system, method and computer implemented process for conducting a variety of assays. More particularly, the instant invention relates to a system, method and computer implemented process for use in analyzing fluid samples. The invention relates even more particularly to calculating or collecting a sample transformation time or any of a variety of sample information by moving a sample over a sensor, during data collection, to dissolve a reagent or to prevent the accumulation of unwanted material on or about the sensor surface.

BACKGROUND OF THE INVENTION

Numerous procedures and techniques exist for analyzing and testing blood and other body fluids. To name one, coagulation techniques may be used to collect a wide variety of information from given samples of blood. While some of these procedures are relatively simple, others can be more sophisticated and require multiple steps or preparations. For instance, many procedures involving blood samples require the addition of reagents to commence the formation of clots or other steps to prepare the sample for data collection and to account for the unique characteristics of blood.

For example, keeping blood in a fluid state, termed hemostasis, requires a subtle balance of pro- and anticoagulants. In the human body, procoagulants prevent excessive bleeding by blocking blood flow from a damaged vessel, whereas anticoagulants prevent clots from forming in the circulating system which could otherwise block blood vessels and lead to myocardial infarction or stroke.

The biochemical sequence leading to a blood clot is termed the coagulation cascade. This mechanism is based on catalytic conversion of fibrinogen, a soluble plasma protein, to insoluble fibrin. The enzyme catalyzing this reaction is thrombin. which does not permanently circulate in the blood in an active form but exists as prothrombin, the inactive precursor of thrombin. Conversion to thrombin occurs in the presence of calcium ions and tissue thromboplastin. This mechanism is known as the extrinsic pathway. A second, more complex, intrinsic pathway is activated by clotting factors associated with platelets.

Diagnosis of hemorrhagic conditions such as hemophilia, where one or more of the twelve blood clotting factors may be defective, can be achieved by a wide variety of coagulation tests. In addition, several tests have been developed to monitor the progress of thrombolytic therapy. Other tests have been developed to signal a prethrombolytic or hypercoagulable state, or to monitor the effect of administering protamine to patients during cardiopulmonary bypass surgery. However, the main value of coagulation tests is in monitoring oral and intravenous anticoagulation therapy. Three of the key diagnostic tests are activated partial thromboplastin time (APTT), prothrombin time (PT), and activated clotting time (ACT).

An APTT test evaluates the intrinsic and common pathways of coagulation. For this reason APTT is often used to monitor intravenous heparin anticoagulation therapy. Specifically, it measures the time for a fibrin clot to form after the activating agent, calcium, and a phospholipid have been added to the citrated blood sample. Heparin administration has the effect of suppressing clot formation.

A PT test evaluates the extrinsic and common pathways of coagulation and, therefore, is used to monitor oral anticoagulation therapy. The oral anticoagulant coumadin suppresses the formation of prothrombin. Consequently, this test is based on the addition of calcium and tissue thromboplastin to the blood sample.

An ACT test evaluates the intrinsic and common pathways of coagulation. It is often used to monitor anticoagulation via heparin therapy. The ACT test is based on addition of an activator to the intrinsic pathway to fresh whole blood to which no exogenous anticoagulant has been added.

The standard laboratory technology for coagulation tests typically uses a turbidimetric method. For analysis, whole-blood samples are collected into a citrate vacutainer and then centrifuged. The assay is performed with plasma to which a sufficient excess of calcium has been added to neutralize the effect of citrate. For a PT test, tissue thromboplastin is provided as a dry reagent that is reconstituted before use. This reagent is thermally sensitive and is maintained at 4 degrees C. Aliquots of sample and reagent are transferred to a cuvette heated at 37 degrees C, and the measurement is made based on a change in optical density.

As an alternative to the turbidimetric method, Beker et al. (See, Haemostasis (1982) 12:73) introduced a chromogenic PT reagent (Thromboquant PT). The assay is based on the hydrolysis of p-nitroaniline from a modified peptide, Tos-Gly-Pro-Arg-pNA, by thrombin and is monitored spectrophotometrically.

Coagulation monitors are known for the analysis of whole blood. For example, a unit-use cartridge has been described in U.S. Pat. No. 4,756,884 in which dry reagents are placed into the analyzer which is then heated to 37 degrees C before a drop of blood is introduced. The sample is mixed with the reagent by capillary draw. The detection mechanism is based on laser light passing through the sample. Blood cells moving along the flow path yield a speckled pattern specific to unclotted blood. When the blood clots, movement ceases producing a pattern specific to clotted blood.

An automatic coagulation timer has been described which measures the activated clotting time (ACT) in blood samples from patients during cardiopulmonary bypass. The sample is added to a cartridge which incorporates a stirring device onto which the clot forms. Motion of the stirring device is controlled by a photo optical detector (See, Keeth et al., Proceedings Am. Acad. Cardiovascular Perfusion (1988) 9:22).

U.S. Pat. No. 4,304,853 discloses the use of a substrate which produces an electroactive product on reaction with the enzyme thrombin. A sensor is used to detect the electroactive product. The disclosure does not include a single-use cartridge and does not disclose the use of a second sensor to monitor the location of the sample.

U.S. Pat. No. 4,497,744 discloses a turbidometric method for assaying coagulation. Plasma containing an excess of citrate is used in the test. A reagent which induces clotting is added, the sample is placed in a turbidometer, and coagulation is indicated by an increase in the turbidity of the sample.

U.S. Pat. No. 5,096,669, incorporated herein by reference, includes the general format for use of a cartridge and analytzer for blood chemistry testing such as potassium and glucose blood levels and the use of a pump to move a sample fluid to a sensor region in a single direction.

U.S. Pat. No. 5,200,051, incorporated herein by reference, discloses efficient methods of microfabrication of sensor devices for analysis of analytes.

U.S. Pat. No. 5,302,348 discloses a blood coagulation test apparatus in which blood is forced to traverse a capillary conduit. When the time for traverse exceeds the previous time by a certain percentage, coagulation is deemed to have occurred. The apparatus includes an unclosed entry port which is connected to two conduits, the first receiving the sample to be assayed, the second receiving overflow sample.

U.S. Pat. Nos. 5,447,440 and 5,628,961, both incorporated herein by reference, disclose a single-use cartridge and reader used in coagulation assays. The condition of the sample is determined by its flow properties as detected, for example, by a conductivity sensor.

U.S. Pat. No. 5,526,111 discloses a method for calculating a coagulation characteristic of a sample of blood, a blood fraction, or a control. This method uses a backwards looking approach to determine a slope of an envelope at each of a number of stored envelope values from which the coagulation characteristic is determined. However, this method uses a fixed or predetermined sampling time and rectifies stored sample values to provide its envelope values. In addition, this method requires storing the envelope values as well as the sampled signal values.

U.S. Pat. Nos. 5,916,522 and 5,919,711 disclose a device which uses ion-specific electrodes to measure ionic activity of fluids including bodily fluids. The fluids are metered and transported within the device by centrifugation and pressurization of the device.

As evident from the above discussion, the majority of blood tests require the addition and dissolution of some sort of reagent into the sample before data collection can commence. Thus, a need exists for a system, method, and computer implemented process which can be used to efficiently and effectively introduce and dissolve a reagent into a sample. Furthermore, as generally true with other types of medical procedures, the speed and time required to complete the tests are of paramount importance. Thus, a need exists also for a system and method which can dissolve or distribute a reagent into a blood sample in a relatively short amount of time.

Also, the compactness and smaller physical size of today's testing devices has directly resulted in limits on the amount of reagent which may be stored in a sampling device. Consequently, a need exists for a system, method, and computer implemented process which can make use of a limited amount of reagent without placing restrictions on the amount of blood to be sampled. In this manner, a relatively small amount of reagent may be used with samples of any volume. On a related note, in situations where limited amounts of reagent are dissolved in relatively larger amounts of sample, a need also exists for a system, method and computer implemented process which is capable of collecting data from only those portions of sample containing the highest amounts of reagent.

In addition, since data collection can be adversely affected by the accumulation of undesirable material contained in blood—a problem familiar to those skilled in the art of collecting electrical and electrochemical measurements in biological fluids, a need exists also for a method, system and computer implemented process which is capable of preventing such an accumulation in the data collection region of the analyzing device.

SUMMARY OF THE INVENTION

Thus, to address these and other needs of the prior art, it is an object of the present invention to provide a novel system, method and computer implemented process for use in analyzing fluid samples by, for example, reciprocatingly and repeatedly moving a sample over a sensor for purposes of calculating a sample transformation time.

It is also an object of the present invention to provide a technique which can be used to efficiently and effectively mix and dissolve a reagent into a sample.

It is another object of the present invention to provide a technique which can dissolve or distribute a reagent into a fluid sample in a relatively short amount of time.

It is yet another object of the present invention to provide a technique which can make use of a limited amount of reagent without placing restrictions on the amount of fluid to be sampled.

It is still another object of the present invention to provide a technique which is capable of collecting data from only those portions of sample containing the highest amounts of reagent.

Further yet, it is another object of the present invention to provide a technique which is capable of preventing an accumulation of unwanted material in a data collection region of an analyzing device.

To meet these and other objects, the present invention contemplates providing a method, system and computer readable medium storing instructions for using a sample analyzing device having a sample retaining area for holding a sample and at least one sensor located at least partially within the sample retaining area. In this embodiment, the at least one sensor has at least one edge which defines a sample detection location and is capable of detecting a presence or an absence of the sample in the sample detection location. The invention further includes: (a) introducing the sample into the sample retaining area; (b) mixing a reagent with the sample to commence formation of a reagent product; (c) upon detecting the absence of the sample from the sample detection location by the at least one sensor, moving an edge of the sample past an edge of the at least one sensor into the sample detection location so that at least a substantial portion of the sample is located therein; (d) upon detecting the presence of the sample in the sample detection location by the at least one sensor, moving the edge of the sample past the edge of the at least one sensor and out of the sample detection location so that less than a substantial portion of the sample is located therein; and (e) preventing an accumulation of material on or about the at least one sensor by repeating steps (c)–(d) until passage of a predetermined period.

In another embodiment, the present invention contemplates providing a system, method and computer readable medium storing instructions for using a sample analyzing device having a sample retaining area for holding a sample and at least one sensor having a sensing surface located at least partially within the sample retaining area. In this embodiment, the at least one sensor is capable of detecting a presence of the sample when the sample is in contact with the sensing surface and of detecting an absence of the sample when the sample is not in contact with the surface. This embodiment further includes: (a) introducing the sample into the sample retaining area; and at least one of steps (b) and (c); (b) mixing a reagent by moving an air-liquid boundary of the sample through a reagent mixing region of the sample retaining area until the reagent is at least substantially dissolved in a vicinity of the air liquid boundary of the sample to form a reagent rich portion of the sample; and (c) preventing an accumulation of material on the sensing surface by moving an air-liquid boundary of the sample over the sensing surface until completion of a sample analysis; and wherein the reciprocating movement includes moving the sample toward the sensing surface until the sensor detects the presence of the sample, and moving the sample away from the sensing surface until the sensor detects the absence of the sample.

In yet another embodiment, the present invention contemplates providing a system, method and computer readable medium storing instructions for calculating a sample transformation time by utilizing a device comprising a sample retaining area and a sensor located at least partially within the sample retaining area to form a data collection region. In this embodiment, the data is collected from the sample when the sample is moved into the data collection region. This embodiment further includes: (a) introducing the sample into the device; (b) mixing a reagent with the sample to commence formation of a reagent product and transformation of the sample; (c) moving the sample into the data collection region; (d) collecting data by the sensor when the sample is moved into the data collection region; (e) moving the sample out of the data collection region; (f) repeating steps (c)–(e) until a sufficient predetermined transformation is detected from the data collected in step (d); (g) extracting reagent product information from the data collected in the collecting step (d); (h) calculating the transformation time by utilizing the reagent product information extracted in the extracting step (g); and wherein the movement steps (c) and (e) prevent the accumulation of material on or about the sensor.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

Other objects of the present invention will be evident to those of ordinary skill, particularly upon consideration of the following detailed description of the preferred embodiments.

NOTATIONS AND NOMENCLATURE

The detailed descriptions which follow may be presented in terms of program procedures executed on computing or processing systems such as, for example, a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits. values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices.

DETAILED DESCRIPTION OF THE PREFERRED EMBODIMENTS

In accordance with the principles of the present invention. a method, system and computer readable medium for using a sample analyzing device are disclosed. More particularly, the present invention includes using a sample analyzing device which has a sample retaining area formed therein and at least one sensor located at least partially within the sample retaining area. The sensor, in turn, is capable of detecting a presence or an absence of the sample within a sample detection location defined by the sensor edges. Advantageously, the present invention includes mixing a reagent by moving an air-liquid boundary, or edge, of the sample through a reagent mixing region of the sample retaining area to dissolve the reagent within the vicinity of the air-liquid boundary. Additionally, the present invention also includes preventing the accumulation of material on or about the sensor by moving, upon detection of the absence of the sample from the sample detection location, an edge of the sample past an edge of the sensor and into the sample detection location. Similarly, upon detection of the presence of the sample in the sample detection location, the invention includes moving the edge of the sample back past the edge of the sensor and out of the sample detection location. Thus, in the above manner, various tests, for instance blood coagulation tests or immunoassays, may be efficiently and effectively performed.

Figure 1:
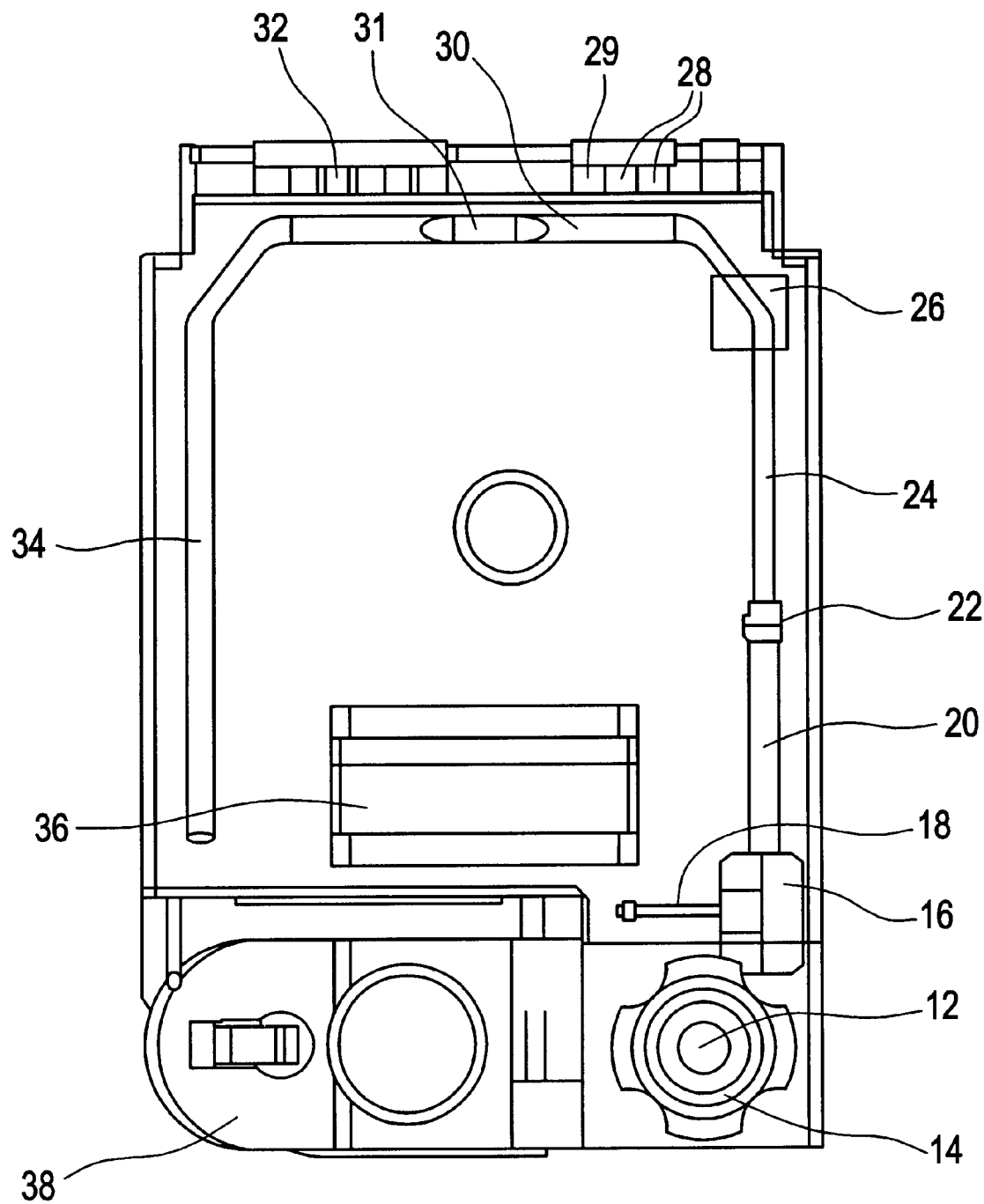
FIG. 1 depicts a cross-sectional plan view of one example of a system capable of implementing and utilizing the techniques of the present invention.

In accordance with the principles of the present invention, one example of a system capable of implementing and utilizing the present invention is depicted in FIG. 1. Furthermore, in addition to the example depicted in FIG. 1, the techniques of the present invention are flexible enough so that they may be implemented and utilized in numerous other devices. For instance, U.S. Pat. Nos. 5,628,961; 5,447, 440; and 5,096,669; and U.S. Provisional Application Ser. No. 60/164,935, all of which are incorporated herein by reference, are directed to various devices for assaying viscosity changes in fluid samples and for performing real time fluid tests, and serve as other examples capable of implementing and utilizing the techniques of the present invention.

Referring to FIG. 1, a cross sectional view of a cartridge or housing 10 implemented according to the principles of the present invention is depicted. A sample entry port 12 allows introduction of a sample into the housing and is surrounded by a circumferential excess sample well 14. A snap cover 38 encloses the sample entry port 12 with the formation of an air-tight seal. Fluidically connected to the sample entry port 12, at one end, is a sample holding chamber or sample retaining area 20. Located at the other end of the sample retaining area 20 is a capillary stop 22.

A pre-sensor channel 24 leads from the capillary stop 22 to an analysis location 31. In addition, a hydrophobic layer 26 is positioned between the pre-sensor channel 24 and the analysis location 31. A reagent and/or a substrate 30 may be deposited or introduced into the system at analysis location 31. Although the reagent 30 is depicted as being downstream of sensors 28 and 29, it is possible to position the reagent 30 upstream of sensors 28 and 29 so that a sample passes through the reagent 30 before reaching the sensors. Furthermore, in communication with the analysis location 31 are one or more conductimetric sensors 28, one or more amperometric sensors 29, and one or more reference sensors 32. Also in communication with the analysis location 31 is a waste tube 34.

A sample may be moved within the system through use of a flexible diaphragm pump 36. Pump 36 facilitates movement of the sample by pumping air through the air tube 18, through overflow chamber 16, and finally into sample retaining area 20. Furthermore, although the pump in FIG. 2 is depicted as being a flexible diaphragm pump, any suitable pump or the like may be used, such as piston and cylinder, electrodynamic, or sonic.

Figure 2:
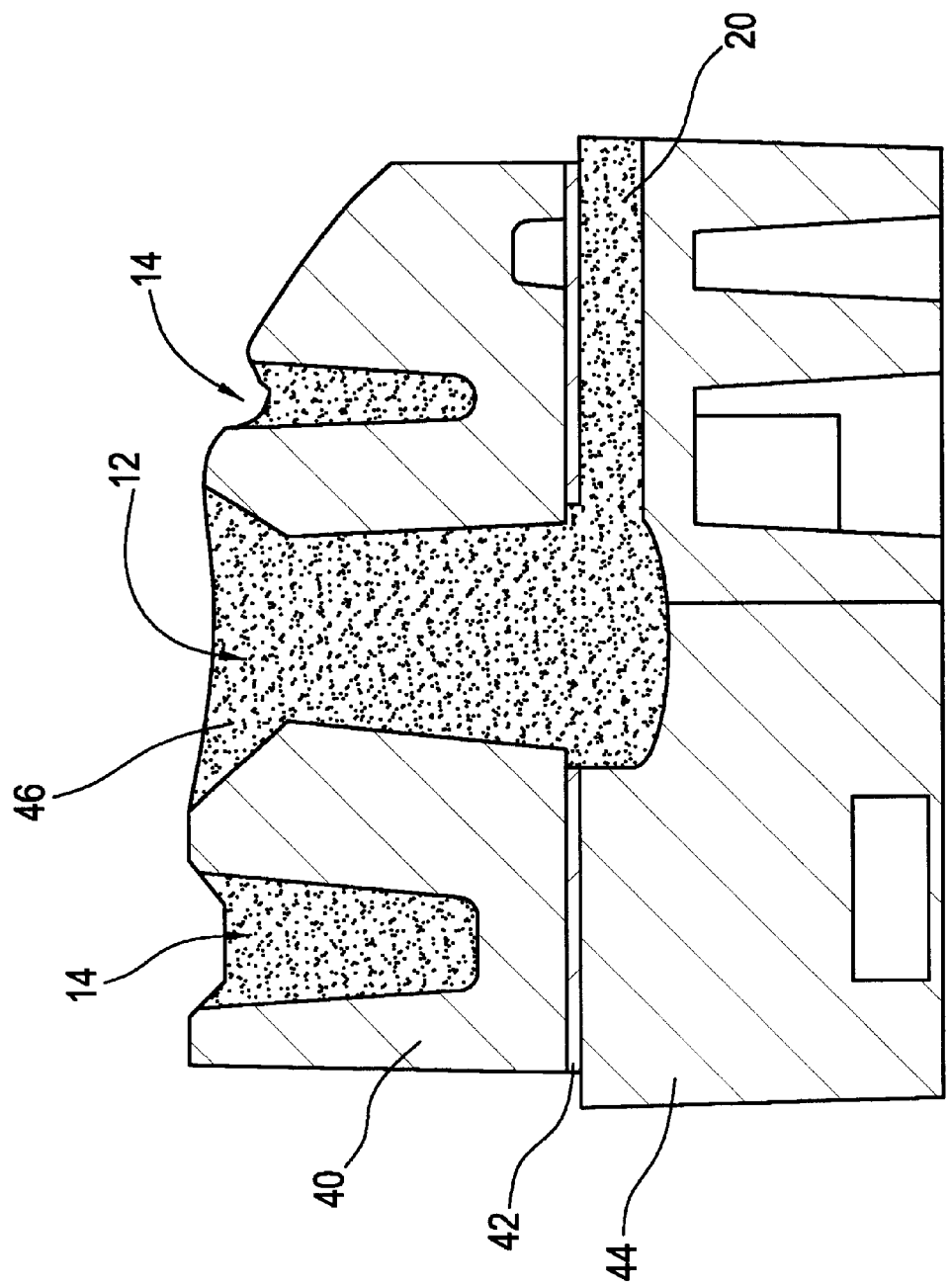
FIG. 2 depicts a cross section of a sample entry port of the system of FIG. 1.

In accordance with the principles of the present invention, FIG. 2 depicts a cross-sectional view of the sample entry port area of the cartridge or housing 10. More specifically, a wall or tape or film 42 is shown interposed between an upper housing 40 and a lower housing of the cartridge. In this regard, tape 42 has an adhesive layer on each side and adheres to the top 40 and base 44 sides of the cartridge. In this particular illustration, the sample entry port 12 as well as the sample retaining area 20 and circumferential well 14 are shown filled with sample 46.

Figure 3:
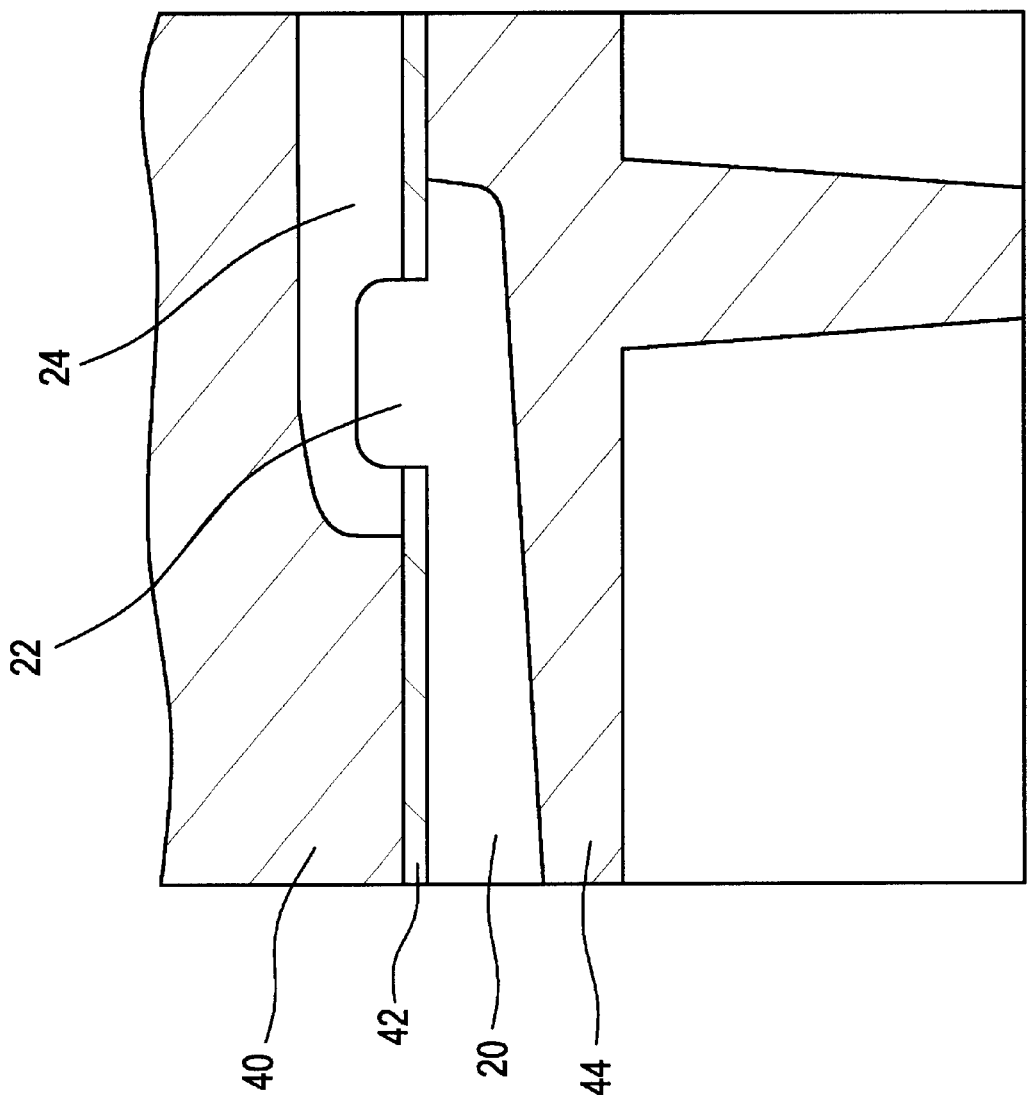
FIG. 3 depicts a cross section of a sample retaining area of the system of FIG. 1.

FIG. 3 depicts a cross-sectional view of the conjunction of the sample retaining area 20, the pre-sensor chamber 24, and the capillary stop 22. As depicted in FIG. 3, sample holding chamber 20 and pre-sensor channel 24 are formed or molded respectively in base 44 and base 40. The tape 42, in turn, forms the top wall of the sample holding chamber 20 and the bottom wall of the pre-sensor chamber 24. Tape 42 is pierced to form a capillary bore or through-hole 22 and functions as a capillary stop by restricting flow between the sample holding chamber 20 and the pre-sensor chamber 24. Although the capillary stop of FIG. 3 is a circular bore or through-hole, other suitable shapes for the capillary stop include rectangular and various irregular shapes. If rectangular in shape, one example has a smallest dimension of about 100 microns to about 400 microns. In such examples, the largest dimension of the capillary stop is about 100 microns to about 1000 microns.

Figure 4:
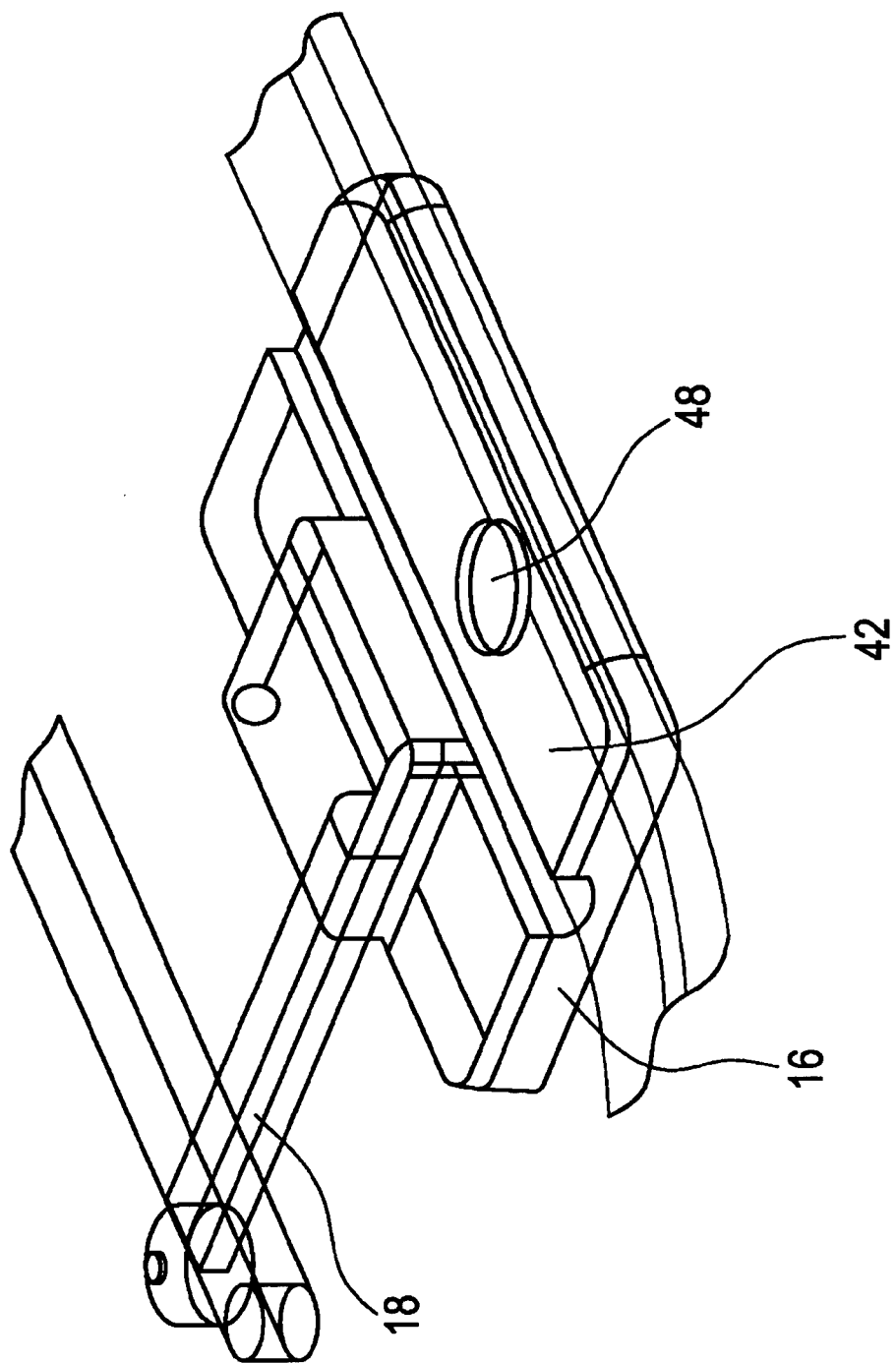
FIG. 4 depicts a perspective view of an overflow chamber of the system of FIG. 1.
Figure 5:
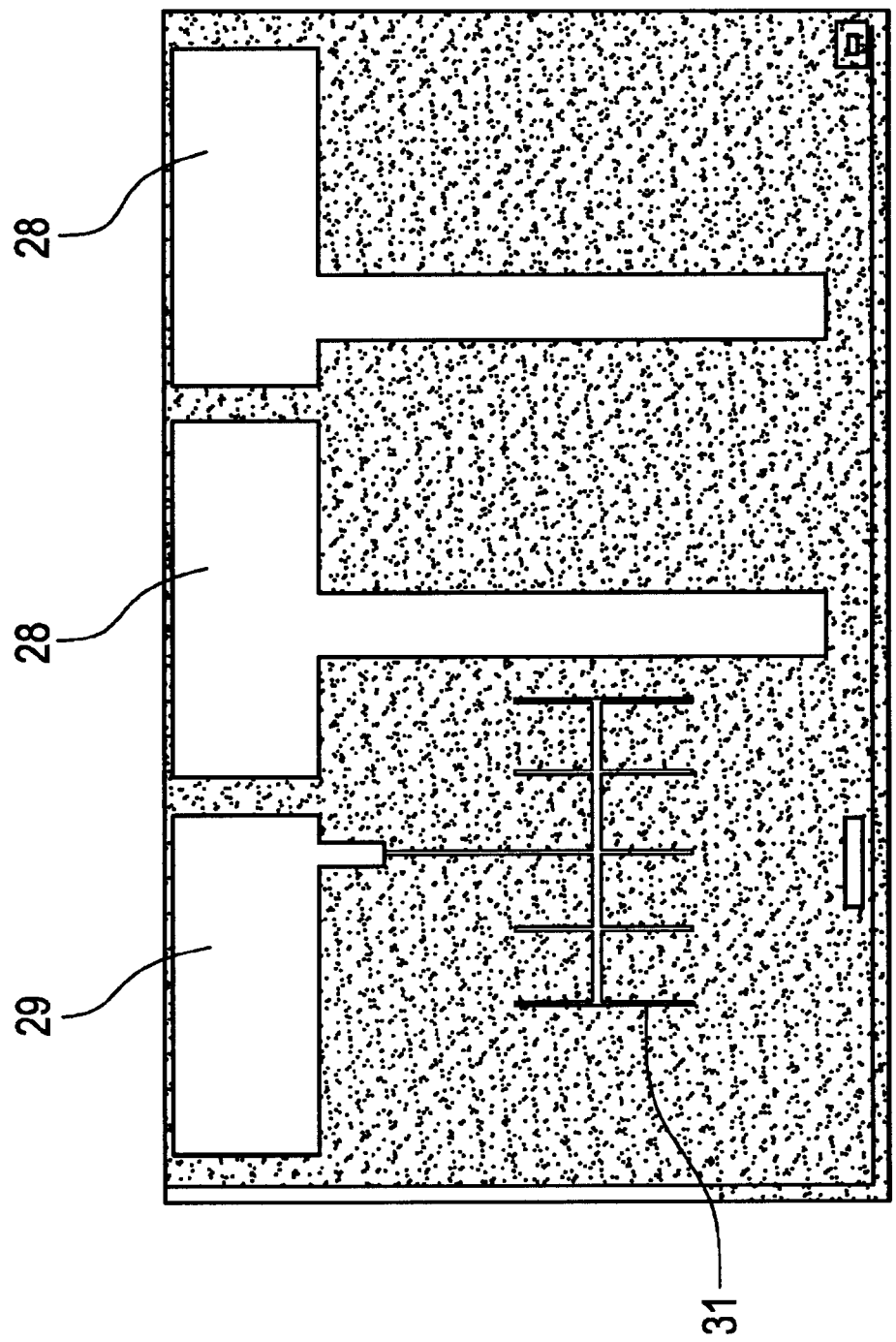
FIG. 5 depicts a conductimetric and amperometric sensor of the system of FIG. 1.

FIG. 4 depicts a perspective view of the overflow chamber 16. In particular, the overflow chamber 16 is located directly above the sample retaining area and has a bottom wall formed by tape 42. An orifice 48 in the tape 42 fluidically connects the overflow chamber 16 to the sample holding chamber 20. The orifice may be any of a circular, rectangular, or irregular shape. The overflow chamber is constructed in the form of a box with relatively low walls. Air tube 18 delivers air from the pump 36 to the overflow chamber 16. The volume of the overflow chamber is in the range of 0.2 microliters to 1 milliliter. A preferred volume of the overflow chamber is in the range of 1 microliter to 10 microliters. The diameter of the circular orifice ranges from about 100 microns to about 1000 microns.

The capillary stop is designed to have a sufficient resistance to stop capillary draw into the pre-sensor channel, but not sufficient to resist sudden pressure changes that occur as the cartridge closure is snapped shut. To reduce the force at the capillary opening at this point, two "overflow" features are incorporated within the cartridge. The first is the overflow well 14 in FIGS. 2 and 3. As the snap closure is shut, some excess sample is pushed into the well rather than into the cartridge. The second feature used to address overflow is orifice 48 or pressure vent, depicted in FIG. 4, through which excess sample may flow into the overflow chamber 16.

As previously discussed, the overflow chamber 16 is a low volume chamber formed in the cartridge top side and located above the sample retaining area, separated from the chamber by a tape 42 wall. The orifice 48 in the tape 42 allows flow of excess sample into the overflow chamber and has a greater area than the opening of the capillary stop. As a result, orifice 48 has a lower flow resistance than the capillary stop mentioned above.

The overflow chamber 16 above the tape opening or orifice 48 has relatively low walls so that once sample is pushed through this hole, it contacts the corona-treated plastic and is drawn into the chamber. The sample displaced as the cartridge is closed is therefore trapped within this chamber. When the air bladder is compressed. air is forced through the air pipe 18 into the overflow chamber 16. The high surface area to volume ratio of this region encourages sample shear so that the air pushes a path through the excess sample leaving the excess sample on the walls of the overflow chamber.

Figure 7:
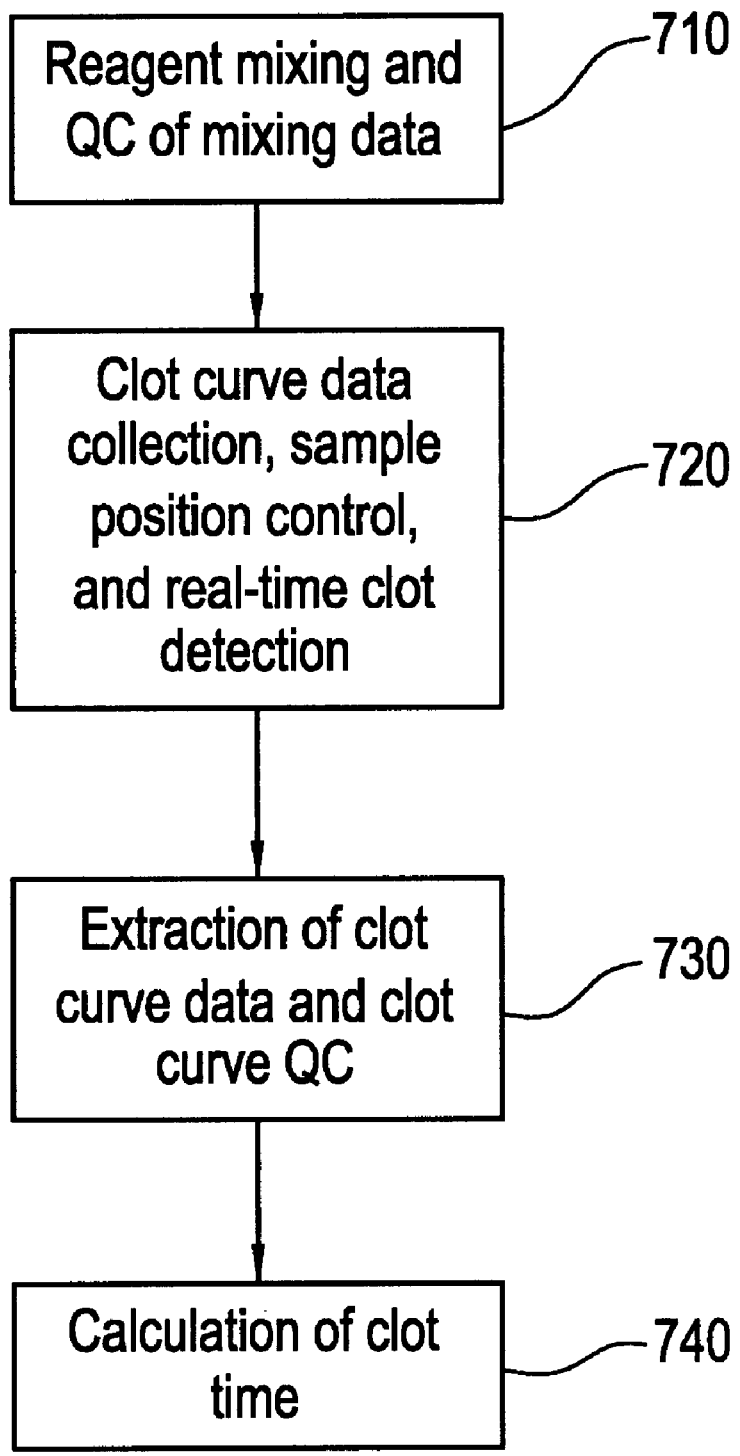
FIG. 7 depicts an example of an overview of a coagulation procedure implementable by the system of FIG. 1.

FIG. 7 depicts a conductimetric sensor 28 and an amperometric sensor 29 located on a sensor chip. This sensor chip, in turn, is positioned at least partially within sample retaining area 20. More specifically, sensor 28 includes two parallel bars or electrodes which together constitute a sensor surface. The electrodes are oriented, in this example, perpendicularly to the length of the sample retaining area or sensor channel. In addition, edges of the sensor surface define a sample detection location within which sensor 29 is capable of detecting the presence or the absence of a sample by measuring a conductivity (or alternatively an electrical resistance) between the two electrodes. By doing so, the sensor 28 may monitor the relative position of the fluid front. At the extremes. an open circuit reading indicates that the fluid has been pushed off the sensor (i.e., the sample is not contiguously covering the electrodes) and a closed circuit reading, on the other hand, indicates the sensor is covered with fluid (i.e., the sample is contiguously covering the electrodes). As will be discussed in greater detail below, movement of the sample, forward and backward, and at a specified velocity may be controlled through use of sensor 28.

In addition to including sensor 28, the present invention may optionally include an amperometric or potentiometric sensor 29. In this example, sensor 29 may be capable of applying a potential and measuring a current through use of its antenna shaped electrode 31. Further, although the sensors in this particular discussion are amperometric and conductimetric sensors, other sensors, for example, any type of electrochemical or potentiometric sensor or the like, may be used. For example, a sensor capable of detecting ion species such as $Na^+$ and $K^+$ may be used. Further, although the sensors in the instant example are depicted as being positioned downstream of the sample retaining area, both of sensors 28 and 29 may be located anywhere within the fluid conduit.

In the example shown in FIG. 7, a potential may be applied to the amperometric sensor 29 with the generation of an electrochemical signal, wherein the signal is proportional to the concentration of the product in the fluid sample. The amperometric sensor has an applied potential of approximately +0.4 V versus a silver-silver chloride electrode and, in another preferred embodiment, the amperometric sensor has an applied potential of approximately +0.1 V versus a silver-silver chloride electrode. The signal generated by the enzyme reaction product at approximately +0.1 V is distinguishable from the signal generated by the unreacted substrate at approximately +0.4 V.

Sample. The coagulation assays commonly performed with the present invention use, for example, a sample of blood, or a sample of a blood derivative such as blood containing an additive or diluent, plasma, serum, or plasma or serum containing an additive or diluent.

Sample Introduction. The sample may be deposited into the system through the sample entry port 12 shown in FIGS. 1 and 2. The entry port 12 is designed so that capillary forces draw a drop of a sample through the port of the system and toward the sample holding chamber. In particular, this drawing action is caused by the geometry and high surface energy of the plastic conduit of the system. The high surface energy is achieved with a corona treatment or equivalent treatment, such as an ion-plasma treatment, before assembly. Once blood reaches the sample retaining area, the geometry and corona-treated surface of the conduit cause the blood to pass along its length up to the capillary stop. As one example, the upper limit of the cross-sectional area of the sample retaining area is that which would prevent capillary draw if the system were to be held upright as it is filled. Also in this example, the lower limit of the cross-section is set to the sample volume required for testing and the reproducibility required of this volume. As one example, the sample holding chamber contains 19 microliters with a cross-sectional area of 0.0075 $cm^2$. In other embodiments the volume of the metered fluid sample is in the range of 1 microliter to 1 milliliter. A preferred volume of the metered fluid sample is in the range of 15 microliters to 50 microliters.

Metering the/fluid sample. The reproducibility of the volume of sample moved into the sensor channel for mixing may affect the reproducibility of the final concentration of dissolved reagent in the blood. In one embodiment, the sample, for instance blood is initially moved into the analysis location 31. The blood sample is then moved forward by air from pump 36 via air pipe 18. The volume of the metered fluid sample will be approximately the volume of the holding chamber 20 between the orifice 48 in the wall of the holding chamber and the capillary stop 22. The volume of blood that is moved depends primarily on the volume of blood in front of the orifice, and secondarily on the surface area-to-volume ratio of the sample-holding chamber. Other factors include the sample hematocrit (the percent of the blood volume comprised of red blood cells), and the fluid speed. These latter three parameters determine the volume of sample that will remain on the walls of the sample retaining area as the chamber is evacuated. The fluid will be metered most precisely at low velocity from a chamber with a low surface-area-to-volume ratio. The lower limit on the sample holding chamber cross-sectional area is determined by the allowable variation in the volume loss to shear at the necessary fluid speed.

To fill the sample holding chamber, a sufficient capillary draw is utilized to provide an adequate amount of sample. In addition, a stop feature is provided to prevent a sample from overflowing into the pre-sensor channel. As discussed above, capillary stop 22 is formed by a small bore or through-hole in the tape gasket 42 between overlapping sections of the sample holding chamber 20 and the pre-sensor channel 24. The capillary stop 22 that is formed is relatively small and has, for example, a thickness equal to that of the tape 42. Although this may decrease the resistance of the capillary and thereby decrease its effectiveness in stopping the fluid, it also minimizes the high shear zone through which the sample must pass before entering the pre-sensor channel. The low volume high-shear region minimizes the loss of sample to the walls of the capillary and decreases the potential for the inclusion of entrapped air segments as the back end of the moving fluid exits the capillary region.

Movement of sample. To move the sample, pump 36 is activated to force air through air pipe 18 into overflow chamber 16 to force a metered amount of sample from the sample retaining area 20 through the pre-sensor channel 24 and into the analysis location 31. In addition, an even flow is effected by ensuring that the surface energy of the conduit is equal on all of its sides (i.e., by using materials having equivalent surface energy or by treating the surfaces to ensure uniformity), thereby preventing the formation of air bubbles within the sample.

Reagent. Depending on the test or analysis to be performed, a variety of components may be included in the reagent, some of which may contribute to rapid redissolving of the reagent by the fluid sample. These include a water-soluble polymer, gelatin, agarose, a polysaccharide, polyethylene glycol, polyglycine, a saccharide, sucrose, an amino acid, glycine, a buffer salt, sodium phosphate, HEPES buffer, or a dye molecule. In addition materials suitable for inducing coagulation via an extrensic pathway may be used including celite, kaolin, diatomaceous earth, clay, silicon dioxide, ellagic acid, natural thromboplastin, recombinant thromboplastin, phospholipid, and mixtures thereof. Furthermore, liquid reagents as well as solid reagents may be used. Finally, the reagent may be initially located in the reagent area, or introduced at any convenient time and at any desired location during testing.

Thrombin-substrate Reaction. In one example, the substrate used in the electrogenic assay has an amide linkage that mimics the thrombin-cleaved amide linkage in fibrinogen. Specifically, the substrate may be a tosyl-glycyl-prolinyl-arginyl-, H-D-phenylalanyl-pipecolyl-, or benzyl-phenylalanyl-valyl-arginyl- moiety attached to a N-phenyl-p-phenylenediamine or N-[p-methoxyphenyl-]-p-phenylenediamine moiety. Thrombin cleaves the amide bond at the carboxy-terminus of the arginine residue or pipecolyl residue because the bond structurally resembles the thrombin-cleaved amide linkage in fibrinogen. The product of the thrombinsubstrate reaction is the electrochemically inert tosyl-glycyl-prolinyl-arginyl-, H-D)-phenylalanylpipecolyl-, or benzyl-phenylalanyl-valyl-arginyl- and the electroactive compounds N-phenyl-p-phenylenediamine or N-[p-methoxyphenyl-]-p-phenylenediamine. The tripeptide sequence is used because it renders the substrate virtually non-reactive with blood proteases other than thrombin and the reactivity of thrombin with the arginine amide linkage in the molecule is very similar to its reactivity with the target amide linkage in fibrinogen. When the substrate is present in a blood or blood derivative sample, generated thrombin simultaneously converts it and fibrinogen to their cleavage products. The electrochemical species reaction product may be detected by, for example, an electrochemical sensor.

There are a wide variety of suitable electrogenic materials which exhibit reversible or quasi-reversible electrochemical reactions which may be assayed using the amperometric sensor of the present system. For example, ferrocene, ferrocyanide, and other organometallic species may be detected. Others include phenazine derivatives. Any suitable electrogenic material may be combined with a suitable substrate for use in assaying an enzyme. For example, suitable electrogenic materials may be combined with a suitable tripeptide with an arginine residue for use in determining the presence of thrombin.

An indicator electrogenic material which is detected at a potential different from the detection potential for the substrate or the electrogenic product of the enzymatic reaction may be included in the reagent. Such a second electrogenic material is useful for standardizing the amperometric sensor. Suitable electrogenic materials for this purpose include ferrocene, terrocyanide, and other organometallic species, phenazine derivatives, N-phenyl-p-phenylenediamine and N-[p-methoxyphenyl-]-p-phenylenediamine.

The test is termed "electrogenic" because the electrochemically detectable species is generated to allow determination of a rate measurement or the test endpoint. This is similar to "chromogenic" or "fluorogenic" endpoint tests in which a change in the light absorbing or emitting properties of a sample indicates the rate measurement or endpoint. In a chromogenic test, for example, the cleaved portion of the substrate molecule is colorless when attached to the tripeptide and brightly colored when liberated by the action of thrombin. By monitoring the wavelength at which the free species absorbs light, the time at which active thrombin is produced can be determined. Chromogenic APTT and PT tests have been shown to have good correlation to traditional APTT and PT plasma tests.

Reagent Mixing. In accordance with the principles of the present invention, the reagent of the system may be rapidly and efficiently mixed. In particular. the system moves an edge or air-liquid interface of the sample repeatedly over the reagent, advantageously promoting reagent dissolution. More specifically, when the sensor determines that the sample is absent from the sample detection location, the sample and its edge are moved toward the sensor surface and into a sample detection location (defined by an edge of the sensor). Likewise, when the sensor determines that the sample is present in the sample detection location, the sample and its edge are moved away from the sensor surface and out of the sample detection location. This procedure is repeated to create an oscillating movement until the reagent is sufficiently dissolved.

Figure 6A:
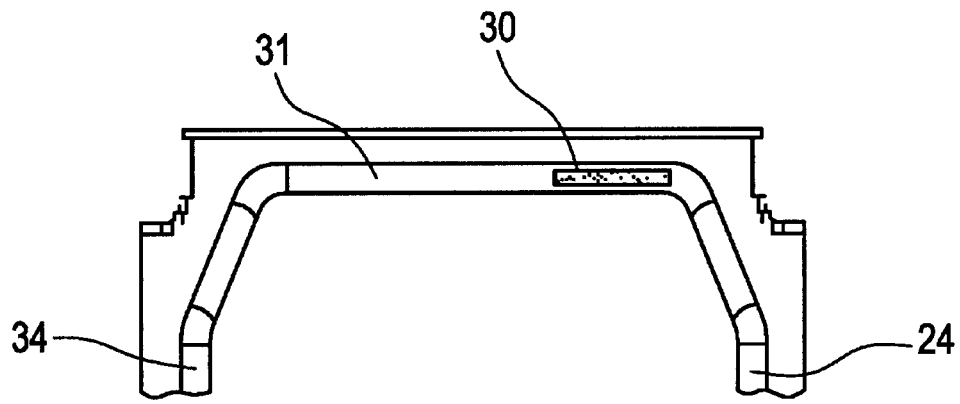
FIGS. 6A–6C depict an oscillating movement of a sample in an analysis location of the system of FIG. 1.
Figure 6B:
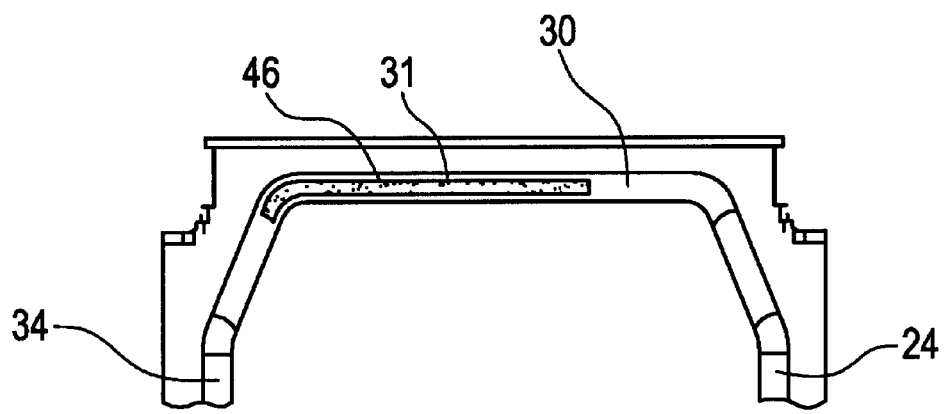
Figure 6C:
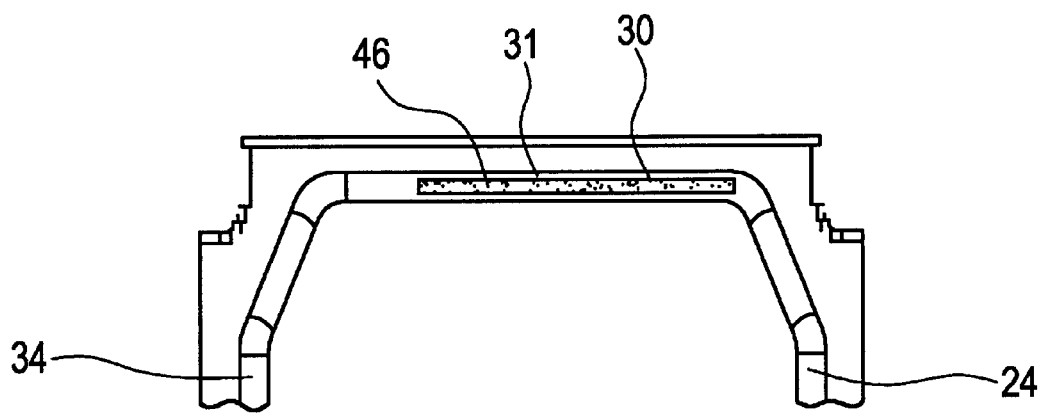

To further illustrate reference is made to FIGS. 6A–6C. In this example, a length of the conduit is coated with reagent 30. Oscillating a segment of the sample over the reagent induces convection thereby rapidly dissolving the reagent. The motion is controlled so that the trailing edge of the blood segment continually moves back and forth across the reagent coating. Furthermore, the movement may occur for any amount of time and is preferably of a length sufficient to dissolve at least a substantial portion of the reagent. In addition, the movement may occur immediately upon the detection of the absence or the presence of the sample, or after a brief amount of time after detection.

FIGS. 6A–C illustrate the analysis location 31 along with other portions of the fluid path including the pre-sensor channel 24 and the waste tube 34. As mentioned above, the reagent may be deposited in the analysis location 31 or introduced any time after the procedure has commenced. FIG. 6B shows sample 46 after its edge has moved past the reagent deposit. Similarly, FIG. 6C shows the sample 46 after its edge has been moved back over the reagent deposit. Although the reagent 30 is shown deposited in the analysis location 31 in FIG. 6A, it is possible to place the reagent at any location along the entire fluid path.

Data Collection and Preventing Accumulation of Unwanted Material on Sensor. In accordance with the principles of the present invention, data is collected through use of, for example, sensor 29. To prevent accumulation of unwanted material on or about the sensor, an edge of the sample is reciprocatingly moved repeatedly over the sensor surface. Examples of unwanted material include biological materials such as dried blood or blood components such as plasma, serum, cells, proteins, other molecules, salts, etc., and/or the physical adsorption of blood components, e.g., proteins, small molecules, molecules containing thiol groups or anything, located on the electrode to block the surface or change its electroactivity.

In one embodiment, the oscillation or reciprocating motion may be at a frequency in the range of 0.2 to 10 Hertz for a period in the range of 1 to 100 seconds. In another embodiment, the oscillation is at a frequency in the range of about 1.5 Hertz for a period of about 20 seconds. In yet another embodiment, the oscillation is at a frequency of about 0.3 Hertz. To gather or extract data, the amperometric or second sensor generates a signal at each oscillation. In this embodiment, the amperometric sensor determines the concentration of the product each time the sample is oscillated past the amperometric sensor.

In this embodiment, a first amperometric sensor signal is stored by the system and subsequent signals from the amperometric sensor are stored and compared with the first and other stored signals in order to determine the maximum rate of change in the amperometric sensor signal. These data are analyzed to determine a fixed fraction of the maximum rate of change of the amperometric sensor signal and used to determine, for example, the coagulation parameter of interest.

In the embodiments of the invention which use the substrates tosyl-glycyl-prolinyl-arginyl-, H-D-phenylalanyl-pipecolyl-, or benzyl-phenylalanyl-valyl-arginyl-moiety attached to a N-phenyl-p-phenylenediamine or N-[p-methoxyphenyl-]-p-phenylenediamine moiety, the intact substrates are detected at a voltage of approximately +0.4 V. The electrogenic reaction products N-phenyl-p-phenylenediamine or N-[p-methoxyphenyl-]-p-phenylenediamine are detected at a voltage of approximately +0.1 V. Thus in these embodiments, the system applies a potential to an amperometric sensor with the generation of an electrochemical signal which is proportional to the concentration of the substrate in the fluid sample. Also, the system applies a potential to an amperometric sensor with the generation of an electrochemical signal which is proportional to the concentration of the product in the fluid sample. After hydrolysis of the substrate by thrombin, a product is formed which reacts at the amperometric sensor with the generation of a signal distinguishable from the signal generated by the substrate.

It should be noted that the exact voltages used to amperometrically detect the substrate and the product will vary depending on the chemical structure of the substrate and product. It is important that the difference in the voltages used to detect the substrate and the product be large enough to prevent interference between the readings. With some substrates, the voltage required to electrochemically detect the substrate is so high as to be beyond practical measurement. In these cases, it is only necessary that the product be detectable amperometrically.

The sensors are preferably microfabricated of any suitable electroconductive material and are preferably made of gold, platinum, silver or iridium. It is also desirable to coat the sensor with a thin organic layer which prevents poisoning of the sensor surface by blood components such as a self-assembled thiol film. Mercaptoalkaniols form self-assembled thiol firms, and some examples include mercaptoethanol, mereaptopropanol, mercaptobutanol, and mixtures thereof.

Thus, by reciprocatingly moving the sample into contact with the sensor and then out of contact with the sensor, the accumulation of unwanted material on the sensor surface may be prevented, thereby resulting in measurements that are more accurate than previously available from the prior art.

Creating a Reagent Rich Portion in the Sample. In accordance with the principles of the present invention, a reagent rich portion may be created in the sample by reciprocatingly moving only a portion of the sample through the reagent mixing area. In this manner, because reagent need not be dissolved in the entire sample, a relatively small amount of reagent may be used without compromising the quality of the performed procedure. More specifically, only a first portion of the sample is moved through the reagent mixing area (i.e., the area where the reagent is introduced or deposited) whereby movement of the remainder of the sample occurs in the fluid conduit outside of the reagent mixing area. As a result, after mixing, the first portion of the sample has a higher reagent concentration than that of the remainder of the sample. Advantageously, the data collected by, for example, sensor 29 from this reagent rich first portion yields results that are much more accurate than the results collected from prior art methods.

Maintaining the fluid position. In accordance with the principles of the invention, quiescence may be maintained within the sample throughout the course of the test. This is achieved through active position control using feedback from the fluid position sensor employed to monitor the mixing and to facilitate data collection. For short duration tests, the resistance (or conductivity) between the bars of the sensor is maintained within a window of a predetermined minimum and a predetermined maximum, or in other words a set number of ohms above the closed circuit reading, until a data point is recorded by the system or the sensor. The sample air-liquid interface is therefore held between the two bars. If the sample drifts back toward the sample-holding chamber, the resistance will decrease until a pre-set limit is triggered causing the system to push the sample forward until the control resistance is again achieved. If the sample drifts toward the waste tube, the resistance will increase causing the system to pull the sample backwards. With the present invention, the fluid front can be maintained within 100 microns of a nominal position. In addition, the movements are of a low enough amplitude and speed as to avoid convection within the sample.

The position control feature of the present invention may advantageously be used in conjunction with the accumulation prevention feature to produce exceptional results. For instance, with coagulation tests that require lengthy amounts of time to produce an endpoint, for example 15 minutes, red blood cells or other unwanted material may settle or blood components may dry on or about the sensor surface. These conditions can cause the resistance for a given fluid position to increase and interfere with the position controller. In the case of settling, the resistance can gradually increase causing the controller to respond as though the fluid has drifted forward causing inaccurate results.

To circumvent these problems, the fluid is periodically moved to the fully closed circuit position where the closed circuit resistance is measured. The fluid is then repositioned at a resistance value offset relative to the new closed circuit reading. This oscillation continually wets the chip to prevent drying and the offset resistance is set relative to the closed circuit reading for the settled sample.

Coagulation Test. In accordance with the principles of the present invention, and as mentioned above, the present techniques and procedures may be utilized to perform a number of fluid and blood tests. As one example, the present invention may be used to determine an amount of time required for a blood sample to coagulate or undergo some other chemical or physical transformation. When blood is used as the sample to be analyzed, the transformation of interest is typically the formation of a blood clot, and the reagent product information is generally a clot curve. As to the actual procedure, referring to FIG. 7, after a blood sample is introduced into the sample retaining area according to, for example, the above procedures, the sample is mixed with the reagent to commence formation of a reagent product 710.

As described above, this mixing includes moving an air-liquid boundary of the sample through a reagent mixing region of the sample retaining area until the reagent is at least substantially dissolved in a vicinity of the air liquid boundary of the sample. Specifically, the reciprocating movement includes moving the sample toward the sensing surface of the sensor until the sensor detects the presence of the sample, followed by moving the sample away from the sensing surface of the sensor until the sensor detects the absence of the sample. Thus, upon detecting the absence of the sample from the sample detection location by the sensor, the system moves an edge of the sample past an edge of the sensor into the sample detection location so that at least a substantial portion of the sample is located therein. Likewise, upon detecting the presence of the sample in the sample detection location by the sensor, the system moves the edge of the sample past the edge of the sensor and out of the sample detection location so that less than a substantial portion of the sample is located therein. Additionally, although in this embodiment movement occurs immediately upon the detection of the presence or the absence of the sample, in alternate embodiments this movement may be delayed to occur a predetermined amount of time after detection.

In addition, this movement may be used to create a reagent rich portion in the sample. More specifically, the mixing movement occurs in a reagent mixing area formed in the sample retaining area. In this embodiment, the mixing includes repeated reciprocating movement through the reagent mixing area by only a first portion of the sample. As a result, movement of a remainder of the sample occurs in the sample retaining area outside of the reagent mixing area. In this manner, the first portion has a higher reagent concentration than that of the remainder. Hence, data may be collected by a sensor from only this first portion of the sample to obtain results that are more accurate than available from prior art devices.

By repeating this movement for a predetermined period of time, for instance long enough to dissolve the reagent, a reagent rich portion is formed in the sample. Through similar repeated movements, that is, moving an air-liquid boundary of the sample over the sensing surface until completion of a sample analysis, an accumulation of material on or about the sensor may also be prevented during data collection 720.

After data collection 720, as will be discussed below, the procedure continues with a step of extracting reagent product information, or in this case, clot curve data 730 and then concludes with the actual calculation of the sample clot time 740.

In accordance with the principles of the present invention, data collection by, for example, the amperometric sensor occurs simultaneously with real-time clot detection and sample position control. In particular, data collection occurs with each movement of the sample into the sample detection location (i.e., the area in the vicinity of the amperometric sensor). These movements continue until a sufficient predetermined transformation of the sample is detected. The transformation can be any kind of chemical or physical change, and in this embodiment is at least the partial formation of a blood clot in the sample.

Figure 8:
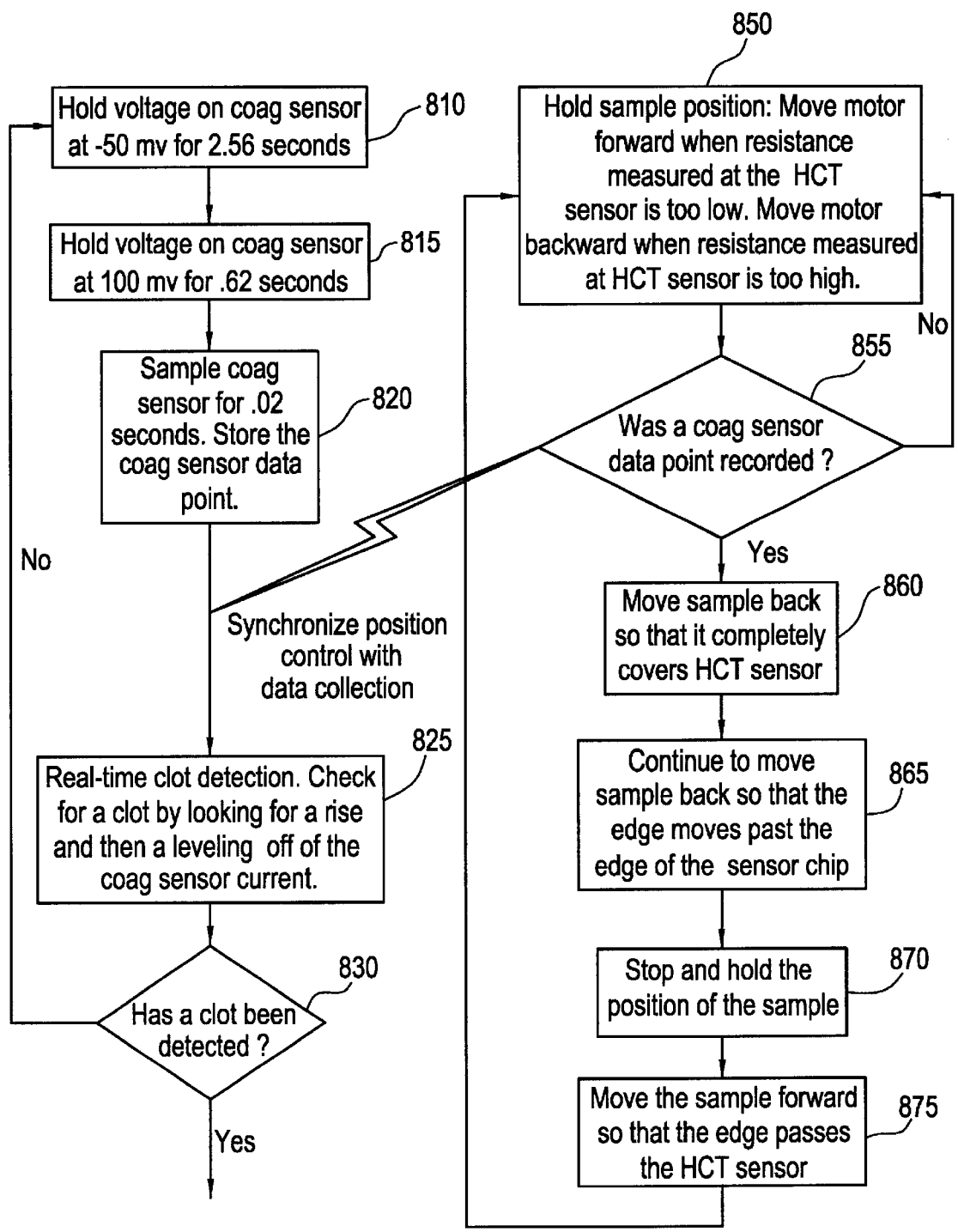
FIG. 8 depicts a data collection step of the procedure of FIG. 7.

Data collection 720 is now discussed in greater detail with reference to FIG. 8. Initially, the voltage on the sensor is held at approximately about −45 to about −55 mV for approximately about 2.5 to about 2.6 seconds 810. The voltage on the sensor is then held at approximately about 95 to about 105 mV for approximately about 0.5 to about 0.6 seconds 815. Subsequently, the sensor is sampled for a predetermined sampling period, for instance about 0.01 to about 0.07 seconds, to collect data on the sample at a single instance 820. This is used to create a data point which is then stored within. for example, system memory.

By varying an electrode potential of the sensor between each instance of data collection, electrochemical contamination of the sensor is prevented. Furthermore, in an alternate embodiment, prior to an initial data sampling, the electrode potential of the sensor may be set to a level that causes electrochemical activity of the sample to remain at a predetermined minimum. Additionally, a Faradaic component of the collected data is maximized by imposing a time delay before collecting data.

After the collection of each data point, reagent product information (i.e., clot curve information) is extracted and analyzed for the real time formation of a blood clot 825. As will he discussed below with reference to FIG. 9, the formation of a blood clot is determined by analyzing the data, basically, for a rise and then a leveling off of the amperometric sensor current 830. If such a condition is not detected, processing resumes with the sampling procedure described above. However if such a condition is detected. the transformation time is calculated by utilizing the extracted reagent product information.

Occurring simultaneously with the data collection is the procedure of maintaining the sample position 850. By facilitating synchronized movement of the sample with data collection, the effects of motion on the sensor may be eliminated. As to this synchronized movement, the sample is moved forward when conductivity measured at the sensor is less than a predetermined minimum. Likewise, the sample is moved backward when the conductivity measured at the sensor is greater than a predetermined maximum. This process is repeated until a sensor data point is recorded by the sensor 855.

Upon indication of a sensor data point, the sample is moved backward to completely cover the sensor surface 860. This movement continues until an edge of the sample moves past an edge of the sensor 865. At that time. movement stops thus holding the position of the sample 870. Subsequently, the sample is moved forward until the sample edge passes the edge of the sensor 875. From there, processing returns to the step of maintaining sample position for the collection of another data point 850.

Figure 9A:
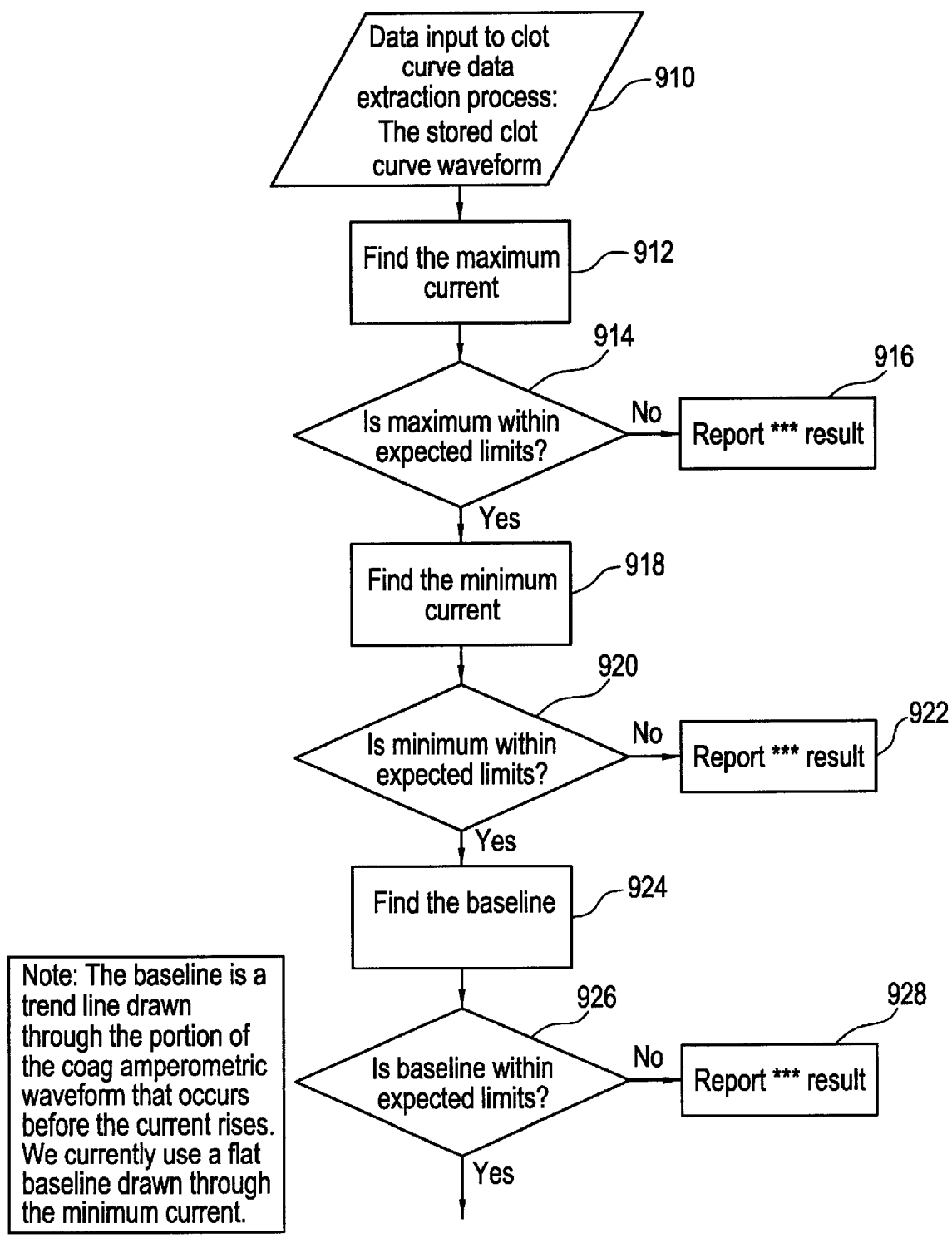
FIGS. 9A–9C depict an information extraction step of the procedure of FIG. 7.
Figure 9B:
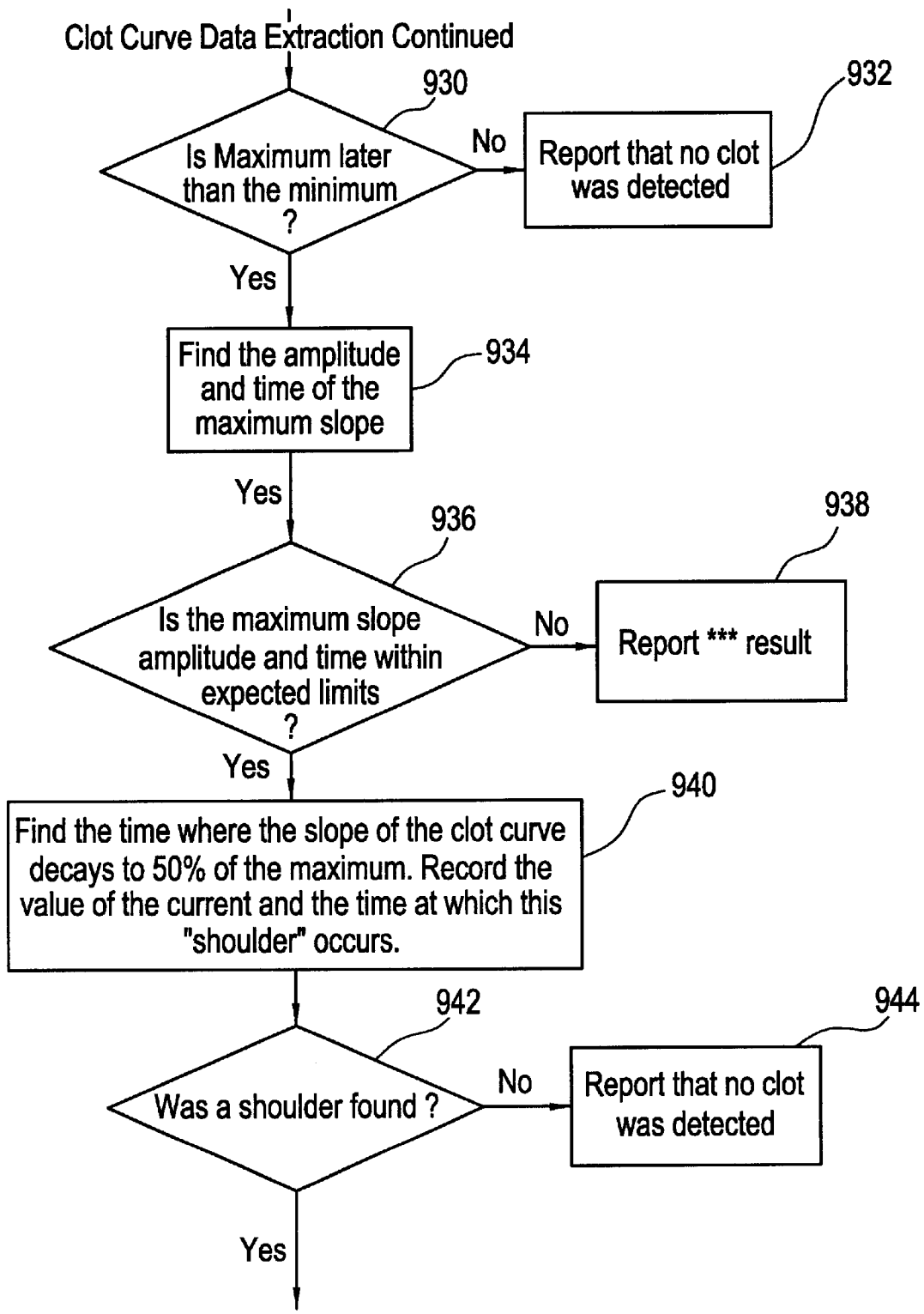
Figure 9C:
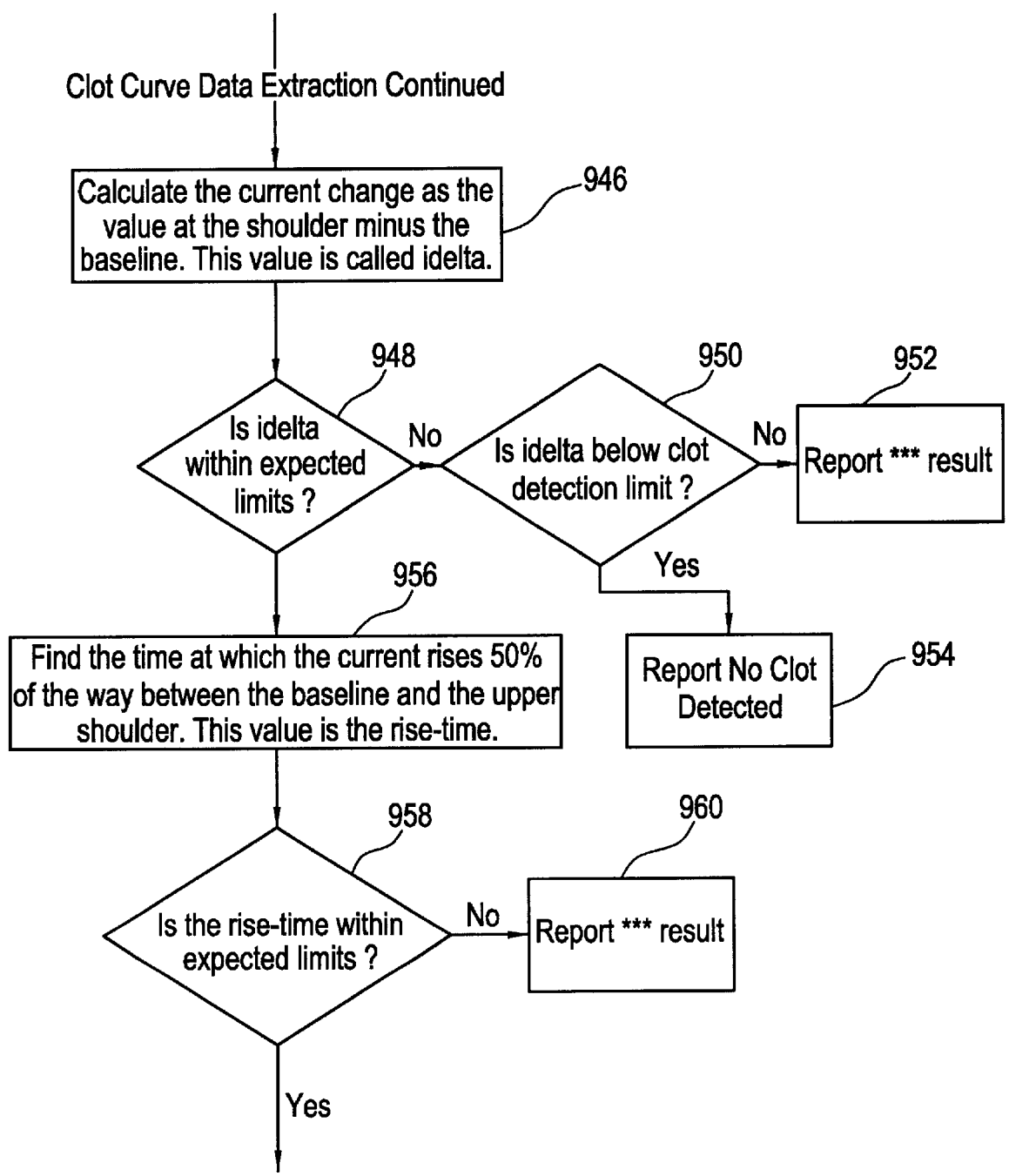

The process of extracting reagent product information from the data to determine a transformation time is now discussed with reference to FIGS. 9A–9C. In this particular example. the process basically calculates a transformation time by utilizing time, slope and amplitude of the clot curve, or in other words, the reagent product information. Specifically, the process utilizes a curve rise time, a maximum slope, and a change in current between a baseline and an upper shoulder, which are defined, respectively, as a trend line drawn through a portion of an amperometric waveform occurring before a current rise and as a point occurring when a slope of a clot curve drops to a predetermined level. Furthermore, the curve rise time is defined as a time at which a current rises to a halfway point between the baseline and the upper shoulder. Even more particularly, the predetermined level defining the shoulder may be approximately about 40% to about 60% of the maximum slope.

Initially, the system accesses data collected in the procedure discussed above from, for example, system memory 910. Then, a maximum current is determined 912. Using this information, a comparison is made between the maximum current and the expected limits of the current 914. Based on this comparison, an error result is reported and the analysis is terminated if the maximum current is not within its expected limits 916. If, however, the maximum current is within the expected limits, processing continues with the determination of a minimum current 918.

Subsequently, a comparison is made between the minimum current and with the current's expected limits 920. If the minimum current is not within the expected limits, an error result is reported and the process is terminated 922. On the other hand, if the minimum current is within the expected limits, processing continues with the determination of a baseline, as discussed below.

After verifying that the maximum and minimum currents are within their expected limits, a baseline is determined 924, which as mentioned above is a trend line drawn through a portion of an amperometric waveform occurring before a current rise. As one example, this baseline may be a flat line drawn through the minimum current. The baseline is then compared with its expected limits 926. Based on this comparison, an error result is reported and the analysis is terminated if the baseline is not within the expected limits 928. In contrast, if the baseline is within its expected limits, processing continues with a comparison between the times of occurrence of the maximum and minimum currents 930.

If the maximum current is found earlier in time than the minimum current, then the absence of clot formation is reported 932. However, if the maximum current is found later in time than the minimum current, the process continues with the determination of an amplitude and a time of the maximum slope 934. From there, both the amplitude and time of maximum slope are compared with their expected limits 936. If the amplitude and time of maximum slope are not within the expected limits, an error result is reported and the process is terminated 938.

Subsequent to the amplitude and maximum slope checks, the system of the present invention calculates the time of the occurrence, if any, of the shoulder, which as discussed above is the point where a slope of the clot curve decays to 50% of the maximum clot curve slope. If such an occurrence is identified, the time of such occurrence as well as the actual current at that time are recorded in, for instance, system memory 940. According to this determination, if a shoulder was not found 942, the absence of clot formation is indicated and the process is terminated 944.

On the other hand, if a shoulder was detected, a current change or idelta is determined by subtracting the baseline current from the shoulder current 946. This idelta, then, is compared with its expected limits 948. If idelta is not within its expected limits, idelta is compared with a clot detection limit 950. Then, if idelta is not within its expected limits and not below the clot detection limit, an error result is indicated and the instant process is terminated 952. If idelta is not within the expected limits but is nevertheless below a clot detection limit, an absence of a clot formation is reported and the process is terminated 954.

Returning to the comparison of idelta with its expected limits 948, if idelta is within its expected limits, a rise time is determined 956. As mentioned above, this rise time is the time at which the current rises to a halfway point between the baseline and the upper shoulder. Next, the rise time is compared with its expected results 958. If the rise time is not within the expected limits an error is reported. Otherwise, the rise time is reported as the clot formation time, and with this final determination, data extraction in this embodiment ends with all relevant data being stored to system memory.

In addition, several other features should be noted. More particularly, the reagents used in the method of the invention may be a substrate for an enzyme in a coagulation cascade. In this case, the reagent product is an electroactive species, and the material to be prevented from accumulating comprises either components of the sample adsorbable onto the surface of a sensor (thus, potentially fouling the sensor) and/or components of a dried form of the sample. In another embodiment of the invention, a sensor may have immobilized on it a receptor, which is capable of binding to a ligand in the sample.

Figure 10:
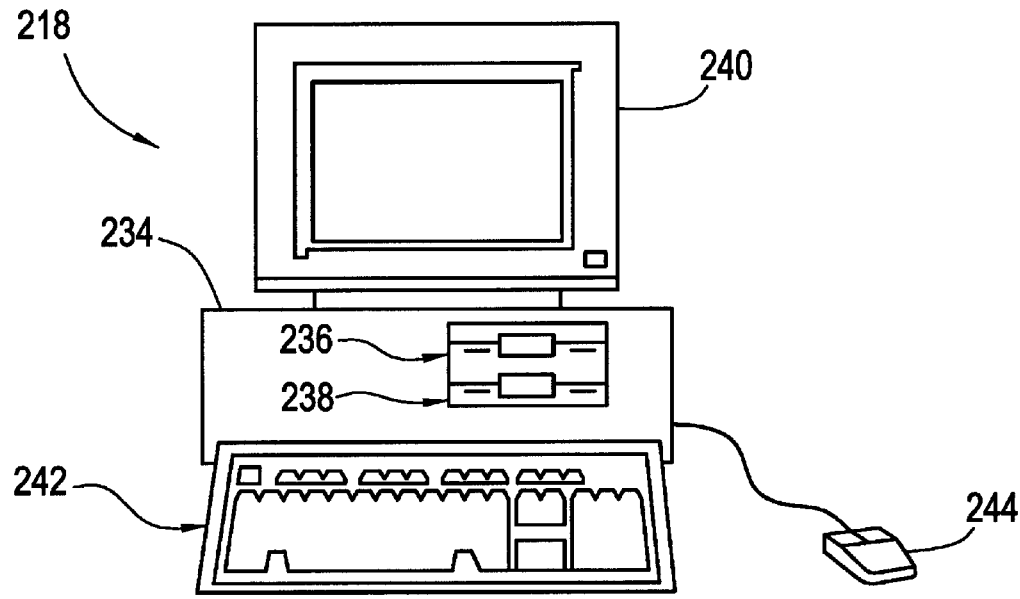
FIG. 10 depicts yet another example of a system capable of implementing and utilizing the techniques of the present invention.

Although the techniques of the present invention as shown as being implemented on the systems described above, it is to be understood that other systems are equally capable of implementing the above features. For example, even though the above systems are intended to be useable as hand-held point-of-care devices, it is also conceivable that the instant invention may be implemented in a computing unit such as that depicted in FIG. 10. In this regard, FIG. 10 is an illustration of a main central processing unit which is also capable of implementing some or all of the computer processing in accordance with a computer implemented embodiment of the present invention. The procedures described herein are presented in terms of program procedures executed on, for example, a computer or network of computers.

Viewed externally in FIG. 10, a computer system designated by reference numeral 218 has a computer 234 having disk drives 236 and 238. Disk drive indications 236 and 238 are merely symbolic of a number of disk drives which might be accommodated by the computer system. Typically, these would include a floppy disk drive 236, a hard disk drive (not shown externally) and a CD ROM indicated by slot 238. The number and type of drives vary, typically with different computer configurations. Disk drives 236 and 238 are in fact optional, and for space considerations, are easily omitted from the computer system used in conjunction with the production process/apparatus described herein.

The computer system also has an optional display 240 upon which information is displayed. In some situations, a keyboard 242 and a mouse 244 are provided as input devices to interface with the central processing unit 234. Then again, for enhanced portability, the keyboard 242 is either a limited function keyboard or omitted in its entirety. In addition, mouse 244 optionally is a touch pad control device, or a track ball device, or even omitted in its entirety as well. In addition, the computer system also optionally includes at least one infrared transmitter and/or infrared received for either transmitting and/or receiving infrared signals, as described below.

Figure 11:
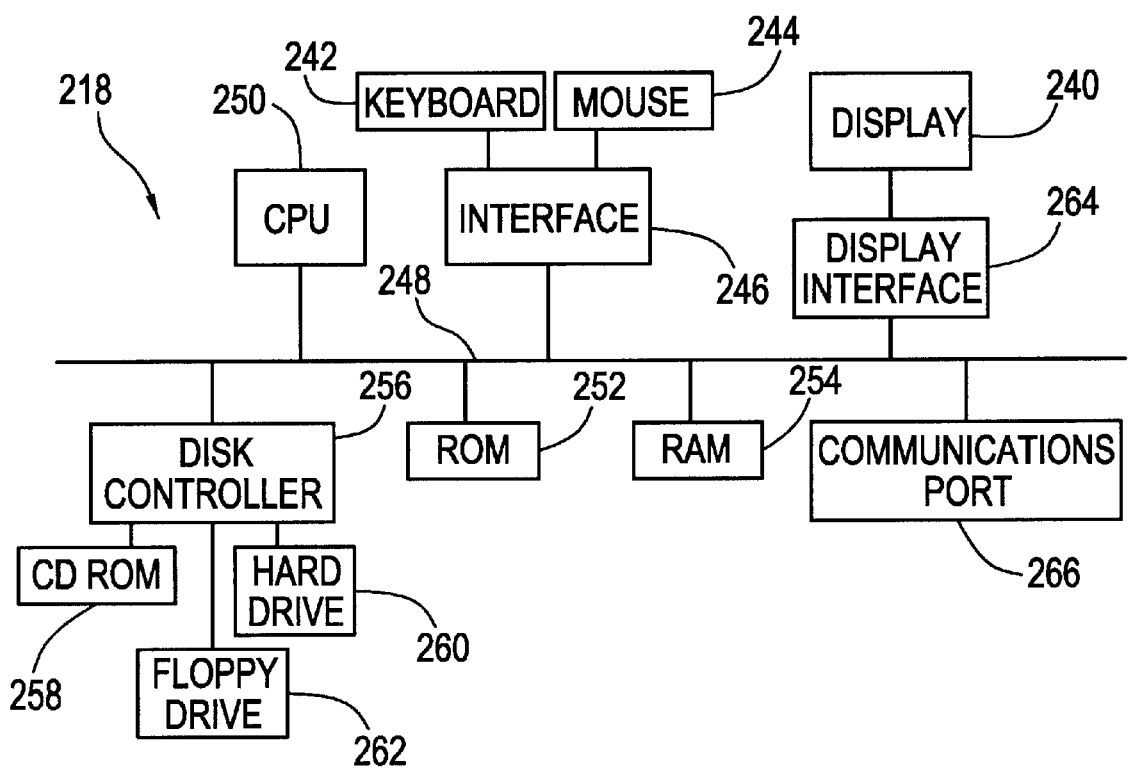
FIG. 11 depicts a block diagram representation of the major components of the system of FIG. 10.

FIG. 11 illustrates a block diagram of the internal hardware of the computer system 218 of FIG. 10. A bus 248 serves as the main information highway interconnecting the other components of the computer system 218. CPU 250 is the central processing unit of the system, performing calculations and logic operations required to execute a program. Read only memory (ROM) 252 and random access memory (RAM) 254 constitute the main memory of the computer. Disk controller 256 interfaces one or more disk drives to the system bus 248. These disk drives are, for example, floppy disk drives such as 262, or CD ROM or DVD (digital video disks) drive such as 258, or internal or external hard drives 260. As indicated previously, these various disk drives and disk controllers are optional devices.

A display interface 264 interfaces display 240 and permits information from the bus 248 to be displayed on the display 240. Again as indicated, display 240 is also an optional accessory. For example, display 240 could be substituted or omitted. Communications with external devices, for example, the other components of the system described herein, occur utilizing communication port 266. For example, optical fibers and/or electrical cables and/or conductors and/or optical communication (e.g., infrared, and the like) and/or wireless communication (e.g., radio frequency (RF), and the like) can be used as the transport medium between the external devices and communication port 266. Peripheral interface 246 interfaces the keyboard 242 and the mouse 244, permitting input data to be transmitted to the bus 248. In addition to the standard components of the computer, the computer also optionally includes an infrared transmitter and/or infrared receiver. Infrared transmitters are optionally utilized when the computer system is used in conjunction with one or more of the processing components/stations that transmits/receives data via infrared signal transmission. Instead of utilizing an infrared transmitter or infrared receiver, the computer system optionally uses a low power radio transmitter and/or a low power radio receiver. The low power radio transmitter transmits the signal for reception by components of the production process, and receives signals from the components via the low power radio receiver. The low power radio transmitter and/or receiver are standard devices in industry.

Figure 12:
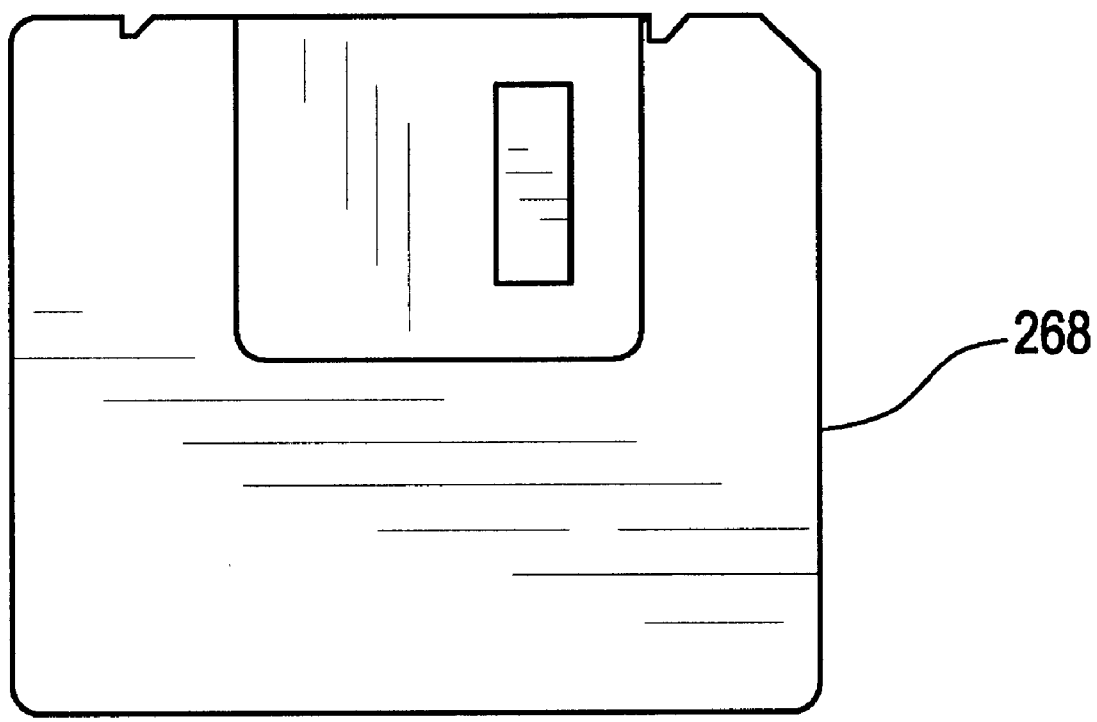
FIG. 12 depicts an example of a memory medium readable by the computing system of FIG. 10 and of storing computer instructions, in accordance with the principles of the present invention.

FIGS. 12 is an illustration of an exemplary memory medium 268 which can be used with disk drives illustrated in FIGS. 10 and 11. Typically, memory media such as floppy disks, or a CD ROM, or a digital video disk will contain, for example, a multi-byte locale for a single byte language and the program information for controlling the computer to enable the computer to perform the functions described herein. Alternatively, ROM 252 and/or RAM 254 illustrated in FIGS. 10 and 11 can also be used to store the program information that is used to instruct the central processing unit 250 to perform the operations associated with the production process.

Although computer system 218 is illustrated having a single processor, a single hard disk drive and a single local memory, the system 218 is optionally suitably equipped with any multitude or combination of processors or storage devices. Computer system 218 is, in point of fact, able to be replaced by, or combined with, any suitable processing system operative in accordance with the principles of the present invention, including sophisticated calculators, and hand-held, laptop/notebook, mini, mainframe and super computers, as well as processing system network combinations of the same.

Conventional processing system architecture is more fully discussed in *Computer Organization and Architecture*, by William Stallings, MacMillan Publishing Co. (3rd ed. 1993); conventional processing system network design is more fully discussed in *Data Network Design*, by Darren L. Spohn, McGraw-Hill, Inc. (1993), and conventional data communications are more fully discussed in *Data Communications Principles*, by R. D. Gitlin, J. F. Hayes and S. B. Weinstain, Plenum Press (1992) and in *The Irwin Handbook of Telecommunications*, by James Harry Green, Irwin Professional Publishing (2nd ed. 1992). Each of the foregoing publications is incorporated herein by reference. Alternatively, the hardware configuration is, for example, arranged according to the multiple instruction multiple data (MIMD) multiprocessor format for additional computing efficiency. The details of this form of computer architecture are disclosed in greater detail in, for example. U.S. Pat. No. 5,163,131; Boxer, A. Where Buses Cannot Go, IEEE Spectrum, February 1995, pp. 41–45; and Barroso, L. A. et al., RPM: A Rapid Prototyping Engine for Multiprocessor Systems, IEEE Computer February 1995, pp. 26–34, all of which are incorporated herein by reference.

In alternate preferred embodiments. the above-identified processor, and, in particular, CPU 250, may be replaced by or combined with any other suitable processing circuits, including programmable logic devices, such as PALs (programmable array logic) and PLAs (programmable logic arrays). DSPs (digital signal processors), FPGAs (field programmable gate arrays), ASICs (application specific integrated circuits), VLSIs (very large scale integrated circuits) or the like.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What we claim is:

1. A method of using a sample analyzing device having a sample retaining area for holding a sample and at least one sensor located at least partially within said sample retaining area, said at least one sensor having at least one edge which defines a sample detection location, said at least one sensor further being capable of detecting a presence or an absence of the sample in said sample detection location, said method comprising the steps of:

(a) introducing the sample into said sample retaining area;

(b) mixing a reagent with the sample to commence formation of a reagent product;

(c) upon detecting the absence of the sample from the sample detection location by said at least one sensor, moving an edge of the sample past an edge of the at least one sensor into said sample detection location so that at least a given portion of the sample is located therein;

(d) upon detecting the presence of the sample in the sample detection location by said at least one sensor, moving the edge of the sample past the edge of the at least one sensor and out of said sample detection location so that less than the given portion of the sample is located therein; and (e) preventing an accumulation of material on or about said at least one sensor by repeating steps (c)–(d) until passage of a predetermined period.

2. The method of claim 1, wherein said at least one sensor comprises two electrodes, wherein said at least one sensor detects the presence of the sample when the sample contiguously covers both electrodes, and wherein said at least one sensor detects the absence of the sample when the sample does not contiguously cover both electrodes.

3. The method of claim 1, wherein said reagent comprises a liquid or a solid reagent.

4. The method of claim 1, wherein said at least one sensor comprises an electrochemical sensor.

5. The method of claim 4, wherein said electrochemical sensor comprises at least one of an amperometric sensor, a potentiometric sensor, or a conductivity sensor.

6. The method of claim 1, wherein said sample analyzing device further comprises another sensor for collecting data from the sample, said method further comprising:
    collecting data by said another sensor when the sample is moved into said sample detection location;
    repeating steps (c)–(d) until a sufficient predetermined transformation of the sample is detected from said collected data;
    extracting reagent product information from said collected data; and
    calculating a transformation time by utilizing said extracted reagent product information.

7. The method of claim 6, wherein said another sensor comprises an electrochemical sensor.

8. The method of claim 7, wherein said electrochemical sensor comprises an amperometric sensor or a potentiometric sensor.

9. The method of claim 6, wherein the predetermined transformation comprises a chemical or physical change.

10. The method of claim 6, wherein the sample comprises blood, wherein the transformation comprises at least a partial formation of a blood clot, and wherein the reagent product information comprises a clot curve, and the transformation time comprises a clot time.

11. The method of claim 6, wherein said another sensor comprises an amperometric sensor capable of applying a potential and measuring a current, and wherein said collecting by said another sensor further comprises the step of collecting said data during a real-time formation of a clot in the sample by detecting a rise and then a leveling off of said amperometric sensor current.

12. The method of claim 6, wherein said another sensor is capable of applying a potential and measuring a current and wherein said step of collecting data by said another sensor comprises:
    holding voltage on said another sensor at approximately about −50 mV for approximately about two and one half seconds;
    holding voltage on said another sensor at approximately about 100 mV for approximately about six-tenths of a second;
    sampling said another sensor for a predetermined sampling period, thereby collecting data on the sample at a single instance and creating a data point; and
    storing said collected data concerning said data point.

13. The method of claim 12, wherein said predetermined sampling period falls in the range of about 0.01 to about 0.07 seconds.

14. The method of claim 6, wherein said reagent product information comprises clot curve information, and wherein extracting reagent product information from said collected data comprises obtaining a rise time, a maximum slope, and a change in current between a baseline and an upper shoulder, wherein said baseline is defined as a trend line drawn through a portion of an amperometric waveform occurring before a current rise, wherein said shoulder is defined as occurring when a slope of a clot curve drops to a predetermined level, and wherein said rise time is defined as a time at which a current rises to a halfway point between said baseline and said upper shoulder.

15. The method of claim 14, wherein said predetermined level defining said shoulder is approximately about 40% to about 60% of said maximum slope.

16. The method of claim 6, wherein said another sensor comprises an amperometric sensor capable of applying a potential and measuring a current, wherein the sample comprises blood, wherein the transformation comprises formation of a blood clot, wherein the reagent product information comprises a clot curve, and wherein extracting reagent product information from said data further comprises the steps of:
    determining a maximum current;
    comparing said maximum current with expected limits, and reporting an error result and terminating said method if said maximum current is not within said expected limits;
    determining a minimum current;
    comparing said minimum current with said expected limits, and reporting an error result and terminating said method if said minimum current is not within said expected limits;
    determining a baseline, wherein said baseline is defined as a trend line drawn through a portion of an amperometric waveform occurring before a current rise;
    comparing said baseline with said expected limits, and reporting an error result and terminating said method if said baseline is not within said expected limits;
    comparing said maximum current with said minimum current, wherein an absence of clot formation is reported if said maximum current is found earlier in time than said minimum current;
    determining an amplitude and a time of a maximum slope;
    comparing said amplitude and said time of said maximum slope with said expected limits, and reporting an error result and terminating said method if said amplitude and said time of said maximum slope are not within said expected limits;
    determining a time, if any, where a slope of a clot curve decays to 50% of a maximum clot curve slope, said time indicating an occurrence of a shoulder, and recording a current at said time and said time itself,
    terminating said method and reporting an absence of clot formation if no shoulder is found;
    determining an idelta by subtracting a baseline current from a shoulder current;
    comparing said idelta with said expected limits, and, if said idelta is not within said expected limits, comparing said idelta with a clot detection limit, and reporting an error result and terminating said method if said idelta is not within said expected limits and not below a clot detection limit, and reporting an absence of a clot formation and terminating said method if said idelta is not within said expected limits but below a clot detection limit;
    determining a rise time, wherein said rise time is defined as a time at which said current rises to a halfway point between said baseline and an upper shoulder; and
    comparing said rise time with said expected results, and reporting an error result if said rise time is not within said expected limits.

17. The method of claim 6, wherein said transformation comprises formation of a blood clot, and wherein said calculating said transformation time comprises utilizing time, slope and amplitude.

18. The method of claim 6, wherein said device further comprises a pump for moving the sample and wherein said at least one sensor is capable of measuring conductivity, said method further comprising the additional steps of:

moving the sample forward when conductivity measured at said at least one sensor is less than a predetermined minimum;

moving the sample backward when conductivity measured at said at least one sensor is greater than a predetermined maximum; and repeating said moving steps until a sensor data point is recorded by said another sensor.

19. The method of claim 6, further comprising eliminating any effects of motion on said another sensor by synchronizing movement of the sample with data collection by said another sensor.

20. The method of claim 6, further comprising collecting data from a reagent rich portion of the sample by reciprocatingly moving the sample over said another sensor.

21. The method of claim 6, wherein the detection of said transformation comprises the detection of a real time formation of at least one clot.

22. The method of claim 6, wherein said another sensor is capable of measuring a current and wherein said collecting data by said another sensor comprises:

holding voltage on said another sensor at approximately about −45 to about −55 mV for approximately about 2.5 to about 2.6 seconds;

holding voltage on said another sensor at approximately about 95 to about 105 mV for approximately about 0.5 to about 0.6 seconds;

sampling said another sensor for approximately about 0.01 to about 0.07 seconds, thereby collecting data on the sample at a single instance and creating a data point; and storing said collected data concerning said data point.

23. The method of claim 6, further comprising, prior to an initial data sampling, setting an electrode potential of said another sensor to a level that causes electrochemical activity of the sample to remain at a predetermined minimum.

24. The method of claim 6, wherein a Faradaic component of the collected data is maximized by imposing a time delay before collecting data.

25. The method of claim 6, wherein electrochemical contamination of said another sensor is prevented by varying an electrode potential of said another sensor between each instance of data collection.

26. The method of claim 1, wherein said mixing step (b) occurs in said sample retaining area and comprises dissolving the reagent into the sample by repeatedly moving the sample into and out of said sample detection location.

27. The method of claim 1, wherein the step of mixing the sample with the reagent comprises repeatedly moving the sample so that an edge of the sample moves past an edge of said at least one sensor and into said sample detection location followed by moving the sample so that the edge of the sample moves back past the edge of said at least one sensor and out of said sample detection location.

28. The method of claim 1, wherein said mixing step (b) comprises moving the sample into said sample detection location when the sample is determined to be absent from said sample detection location by said at least one sensor, and moving the sample out of said sample detection location when the sample is determined to be present in said sample detection location by said at least one sensor.

29. The method of claim 1, wherein said device has a reagent mixing area formed in said sample retaining area, and wherein said mixing step (b) comprises repeated reciprocating movement through said reagent mixing area of only a first portion of the sample whereby movement of a remainder of the sample occurs in said sample retaining area outside of said reagent mixing area, wherein after said mixing, said first portion has a higher reagent concentration than that of said remainder.

30. The method of claim 29, wherein said sample analyzing device further comprises another sensor capable of collecting data from the sample, said method further comprising collecting data from the sample by said another sensor only from said first portion of the sample.

31. The method of claim 29, wherein the reagent is initially located in said reagent mixing area.

32. The method of claim 29, wherein the reagent is introduced into said reagent mixing area during said mixing step (b).

33. The method of claim 1, wherein said movement in said moving steps (c) and (d) commences a predetermined amount of time after detection of the presence or absence of the sample in said sample detection location.

34. The method of claim 1, wherein said movement in said moving steps (c) and (d) commences substantially immediately after detection of the presence or absence of the sample in said sample detection location.

35. The method of claim 1, wherein the reagent is a substrate for an enzyme in a coagulation cascade, wherein the reagent product is an electroactive species, and wherein said material to be prevented from accumulating comprises at least one or more adsorbable components of the sample or a dried form of the sample.

36. A method of using a sample analyzing device having a sample retaining area for holding a sample and at least one sensor having a sensing surface located at least partially within said sample retaining area, said at least one sensor being capable of detecting a presence of the sample when the sample is in contact with the sensing surface and of detecting an absence of the sample when the sample is not in contact with the surface by a reciprocating movement, said method comprising the steps of:

(a) introducing the sample into said sample retaining area; and (b) mixing a reagent by moving an air-liquid boundary of the sample through a reagent mixing region of said sample retaining area until the reagent is at least substantially dissolved in a vicinity of the air liquid boundary of the sample to form a reagent rich portion of the sample;

wherein said reciprocating movement comprises moving the sample toward the sensing surface until the sensor detects the presence of the sample, and moving the sample away from the sensing surface until the sensor detects the absence of the sample.

37. The method of claim 36, further comprising the step of:

preventing an accumulation of material on said sensing surface by moving an air-liquid boundary of the sample over said sensing surface until completion of a sample analysis.

38. A computer readable medium storing instructions for using a sample analyzing device having a sample retaining area for holding a sample and at least one sensor located at least partially within said sample retaining area, said at least one sensor having at least one edge which defines a sample detection location, said at least one sensor further being capable of detecting a presence or an absence of the sample in said sample detection location, said instructions being executable by a computer and comprising the steps of:

(a) introducing the sample into said sample retaining area;

(b) mixing a reagent with the sample to commence formation of a reagent product;

(c) upon detecting the absence of the sample from the sample detection location by said at least one sensor, moving an edge of the sample past an edge of the at least one sensor into said sample detection location so that at least a given portion of the sample is located therein;

(d) upon detecting the presence of the sample in the sample detection location by said at least one sensor, moving the edge of the sample past the edge of the at least one sensor and out of said sample detection location so that less than the given portion of the sample is located therein; and (e) preventing an accumulation of material on or about said at least one sensor by repeating steps (c)–(d) until passage of a predetermined period.

39. A computer readable medium storing instructions for using a sample analyzing device having a sample retaining area for holding a sample and at least one sensor having a sensing surface located at least partially within said sample retaining area, said at least one sensor being capable of detecting a presence of the sample when the sample is in contact with the sensing surface and of detecting an absence of the sample when the sample is not in contact with the surface by a reciprocating movement, said instructions being executable by a computer and comprising the steps of:

(a) introducing the sample into said sample retaining area; and (b) mixing a reagent by moving an air-liquid boundary of the sample through a reagent mixing region of said sample retaining area until the reagent is at least substantially dissolved in a vicinity of the air liquid boundary of the sample to form a reagent rich portion of the sample;

wherein said reciprocating movement comprises moving the sample toward the sensing surface until the sensor detects the presence of the sample, and moving the sample away from the sensing surface until the sensor detects the absence of the sample.

40. The computer readable medium of claim 39, further comprising the step of:

preventing an accumulation of material on said sensing surface by moving an air-liquid boundary of the sample over said sensing surface until completion of a sample analysis.

41. A system for analyzing a sample and usable with a computer, comprising:

a sample analyzing device having a sample retaining area for holding a sample and at least one sensor located at least partially within said sample retaining area, said at least one sensor having at least one edge which defines a sample detection location, said at least one sensor further being capable of detecting a presence or an absence of the sample in said sample detection location; and a memory medium readable by the computer and storing computer instructions, the instructions comprising the steps of:

(a) introducing the sample into said sample retaining area;

(b) mixing a reagent with the sample to commence formation of a reagent product;

(c) upon detecting the absence of the sample from the sample detection location by said at least one sensor, moving an edge of the sample past an edge of the at least one sensor into said sample detection location so that at least a given portion of the sample is located therein;

(d) upon detecting the presence of the sample in the sample detection location by said at least one sensor, moving the edge of the sample past the edge of the at least one sensor and out of said sample detection location so that less than the given portion of the sample is located therein; and (e) preventing an accumulation of material on or about said at least one sensor by repeating steps (c)–(d) until passage of a predetermined period.

42. A system for analyzing a sample and useable with a computer, comprising:

an analyzing device having a sample retaining area for holding a sample and at least one sensor having a sensing surface located at least partially within said sample retaining are, said at least one sensor being capable of detecting a presence of the sample when the sample is in contact with the sensing surface and of detecting an absence of the sample when the sample is not in contact with the surface by a reciprocating movement; and a memory medium readable by the computer and storing computer instructions, the instructions comprising the steps of:

(a) introducing the sample into said sample retaining area; and (b) mixing a reagent by moving an air-liquid boundary of the sample through a reagent mixing region of said sample retaining area until the reagent is at least substantially dissolved in a vicinity of the air liquid boundary of the sample to form a reagent rich portion of the sample;

wherein said reciprocating movement comprises moving the sample toward the sensing surface until the sensor detects the presence of the sample, and moving the sample away from the sensing surface until the sensor detects the absence of the sample.

43. The system of claim 42, further comprising the step of:

preventing an accumulation of material on said surface by moving an air-liquid boundary of the sample over said sensing surface until completion of a sample analysis.

44. A method for calculating a sample transformation time by utilizing a device comprising a sample retaining area and a sensor located at least partially within the sample retaining area to form a data collection region, wherein data is collected from the sample when the sample is moved into said data collection region, said method comprising the steps of:

(a) introducing the sample into said device;

(b) mixing a reagent with the sample to commence formation of a reagent product and transformation of the sample;

(c) moving the sample into said data collection region;

(d) collecting data by said sensor when the sample is moved into said data collection region;

(e) moving the sample out of said data collection region;

(f) repeating steps (c)–(e) until a sufficient predetermined transformation is detected from said data collected in said step (d);

(g) extracting reagent product information from said data collected in said collecting step (d);

(h) calculating the transformation time by utilizing said reagent product information extracted in said extracting step (g); and wherein said movement steps (c) and (e) prevent the accumulation of material on or about said sensor.

45. A method of using a sample analyzing device having a sample retaining area for holding a sample and at least one sensor having a sensing surface located at least partially within said sample retaining area, said at least one sensor being capable of detecting a presence of the sample when the sample is in contact with the sensing surface and of detecting an absence of the sample when the sample is not in contact with the surface by a reciprocating movement, said method comprising the steps of:

(a) introducing the sample into said sample retaining area; and (b) preventing an accumulation of material on said sensing surface by moving an air-liquid boundary of the sample over said sensing surface until completion of a sample analysis;

wherein said reciprocating movement comprises moving the sample toward the sensing surface until the sensor detects the presence of the sample, and moving the sample away from the sensing surface until the sensor detects the absence of the sample.

46. A computer readable medium storing instructions for using a sample analyzing device having a sample retaining area for holding a sample and at least one sensor having a sensing surface located at least partially within said sample retaining area, said at least one sensor being capable of detecting a presence of the sample when the sample is in contact with the sensing surface and of detecting an absence of the sample when the sample is not in contact with the surface by a reciprocating movement, said instructions being executable by a computer and comprising the steps of:

(a) introducing the sample into said sample retaining area; and (b) preventing an accumulation of material on said sensing surface by moving an air-liquid boundary of the sample over said sensing surface until completion of a sample analysis;

wherein said reciprocating movement comprises moving the sample toward the sensing surface until the sensor detects the presence of the sample, and moving the sample away from the sensing surface until the sensor detects the absence of the sample.

47. A system for analyzing a sample and useable with a computer, comprising:

an analyzing device having a sample retaining area for holding a sample and at least one sensor having a sensing surface located at least partially within said sample retaining are, said at least one sensor being capable of detecting a presence of the sample when the sample is in contact with the sensing surface and of detecting an absence of the sample when the sample is not in contact with the surface by a reciprocating movement; and a memory medium readable by the computer and storing computer instructions, the instructions comprising the steps of:

(a) introducing the sample into said sample retaining area; and (b) preventing an accumulation of material on said surface by moving an air-liquid boundary of the sample over said sensing surface until completion of a sample analysis;

wherein said reciprocating movement comprises moving the sample toward the sensing surface until the sensor detects the presence of the sample, and moving the sample away from the sensing surface until the sensor detects the absence of the sample.

* * * * *